United States Patent
Pulliam et al.

(10) Patent No.: US 12,011,595 B2
(45) Date of Patent: Jun. 18, 2024

(54) CONTROL PULSES AND POSTURE FOR ECAPs

(71) Applicant: Medtronic, Inc., Minneapolis, MN (US)

(72) Inventors: Christopher L. Pulliam, Plymouth, MN (US); David A. Dinsmoor, North Oaks, MN (US); Hank Bink, Golden Valley, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 670 days.

(21) Appl. No.: 17/100,455

(22) Filed: Nov. 20, 2020

(65) Prior Publication Data

US 2021/0187297 A1    Jun. 24, 2021

Related U.S. Application Data

(60) Provisional application No. 62/950,777, filed on Dec. 19, 2019.

(51) Int. Cl.
  *A61N 1/36* (2006.01)
(52) U.S. Cl.
  CPC ..... *A61N 1/36062* (2017.08); *A61N 1/36139* (2013.01); *A61N 1/36153* (2013.01); *A61N 1/36192* (2013.01)
(58) Field of Classification Search
  CPC ............ A61N 1/36062; A61N 1/36064; A61N 1/36067; A61N 1/36071; A61N 1/36107;
  (Continued)

(56) References Cited

U.S. PATENT DOCUMENTS 8,515,549 B2   8/2013  Panken et al.
8,958,885 B2   2/2015  Panken et al.
(Continued)

FOREIGN PATENT DOCUMENTS

CN   105792745 A   7/2016
EP     3357533 A1  8/2018
(Continued)

OTHER PUBLICATIONS

Schade et al., "Automatic Adaptation of Neurostimulation Therapy in Response to Changes in Patient Position: Results of the Posture Responsive Spinal Cord Stimulation (PRS) Research Study," Pain Physician, vol. 14, No. 5, Sep./Oct. 2011, pp. 407-417.
(Continued)

*Primary Examiner* — Carl H Layno
*Assistant Examiner* — Jane C Kalinock
(74) *Attorney, Agent, or Firm* — Shumaker & Sieffert, P.A.

(57) ABSTRACT

Systems, devices, and techniques for adjusting electrical stimulation based on a posture state of a patient are described. For example, processing circuitry is configured to control delivery of a first informed stimulation pulse defined by at least a first value of an informed stimulation parameter, control delivery of a control stimulation pulse to a patient, the control stimulation pulse defined by at least a first value of a control stimulation parameter, determine a characteristic value of the ECAP signal elicited from the control stimulation pulse, receive, from a sensor, a posture state signal representing a posture state of the patient, and adjust, based on the characteristic value of the ECAP signal and the posture state signal, the first value of the informed stimulation parameter to a second value of the informed stimulation parameter.

33 Claims, 14 Drawing Sheets

(58) Field of Classification Search
CPC ............ A61N 1/36139; A61N 1/36153; A61N 1/36192; A61B 5/1116; A61B 5/383
USPC .......................................................... 607/72
See application file for complete search history.

(56) References Cited

U.S. PATENT DOCUMENTS

| | | | |
|---|---|---|---|
| 9,084,900 | B2 | 7/2015 | Hershey et al. |
| 9,302,112 | B2 | 4/2016 | Bornzin et al. |
| 9,381,356 | B2 | 7/2016 | Parker et al. |
| 9,511,231 | B1 | 12/2016 | Kent et al. |
| 9,533,148 | B2 | 1/2017 | Carcieri |
| 9,592,387 | B2 | 3/2017 | Skelton et al. |
| 10,183,168 | B2 | 1/2019 | Baru et al. |
| 10,327,654 | B2 | 6/2019 | Strahl et al. |
| 2011/0270134 | A1 | 11/2011 | Skelton |
| 2014/0277282 | A1 | 9/2014 | Jaax |
| 2015/0032181 | A1 | 1/2015 | Baynham et al. |
| 2015/0173636 | A1 | 6/2015 | Mokeke et al. |
| 2015/0360031 | A1 | 12/2015 | Bornzin et al. |
| 2016/0157769 | A1 | 6/2016 | Min et al. |
| 2016/0287126 | A1 | 10/2016 | Parker et al. |
| 2017/0135624 | A1 | 5/2017 | Parker |
| 2017/0361101 | A1 | 12/2017 | Single |
| 2018/0126169 | A1 | 5/2018 | Hou et al. |
| 2019/0168000 | A1 | 6/2019 | Laird-Wah |
| 2019/0175904 | A1 | 6/2019 | Baru et al. |

FOREIGN PATENT DOCUMENTS

| | | | | |
|---|---|---|---|---|
| EP | 3024540 | B1 | 10/2018 | |
| JP | 2018513714 | A | 5/2018 | |
| WO | 2012155188 | A1 | 11/2012 | |
| WO | 2015013398 | A1 | 1/2015 | |
| WO | 2016161484 | A2 | 10/2016 | |
| WO | 2017100866 | A1 | 6/2017 | |
| WO | 2017173493 | A1 | 10/2017 | |
| WO | 2017219096 | A1 | 12/2017 | |
| WO | 2018053336 | A1 | 3/2018 | |
| WO | WO-2018053336 | A1 * | 3/2018 | ........... A61N 1/0551 |
| WO | 2019246579 | A1 | 12/2019 | |
| WO | 2019246582 | A1 | 12/2019 | |

OTHER PUBLICATIONS

U.S. Appl. No. 17/100,384, filed Nov. 20, 2020, by Pulliam et al.
Response to Office Action dated Jan. 9, 2023 from U.S. Appl. No. 17/100,384, filed May 9, 2023, 14 pp.
Office Action from U.S. Appl. No. 17/100,384 dated Jan. 9, 2023, 20 pp.
International Search Report and Written Opinion of International Application No. PCT/US2020/063693, dated Mar. 23, 2021, pp. 13 pp.
Final Office Action from U.S. Appl. No. 17/100,384 dated Jul. 10, 2023, 18 pp.
Office Action from U.S. Appl. No. 17/100,384 dated Sep. 29, 2023, 18 pp.
Response to Final Office Action dated Jul. 10, 2023 from U.S. Appl. No. 17/100,384, filed Sep. 11, 2023, 13 pp.
Response to Office Action dated Sep. 29, 2023 from U.S. Appl. No. 17/100,384, filed Dec. 21, 2023, 14 pp.
Notice of Allowance from U.S. Appl. No. 17/100,384 dated Apr. 10, 2024, 7 pp.

* cited by examiner

CONTROL PULSES AND POSTURE FOR ECAPs

This application claims the benefit of U.S. Provisional Patent Application No. 62/950,777 filed on Dec. 19, 2019, the entire content of which is incorporated herein by reference.

TECHNICAL FIELD

This disclosure generally relates to electrical stimulation, and more specifically, control of electrical stimulation.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered by the medical device as a train of pulses, and the values of the parameters defining the pulses may be altered.

SUMMARY

In general, systems, devices, and techniques are described for managing the delivery of electrical stimulation based on evoked compound action potential (ECAP) signals sensed from a patient. When a patient moves, the distance between implanted electrodes and target nerves changes. For example, electrodes implanted along the spinal column are closer to the spinal cord when a subject lies in a supine posture state as compared to a standing posture state. Similarly, the implanted electrodes may move closer to the spinal cord when a subject coughs or sneezes. This changing distance between the electrodes and target tissue affects neural recruitment for a given intensity of delivered stimulation and can cause the patient's perception and/or therapeutic benefit to also change. Therefore, a characteristic value of the ECAP signal can represent the change in distance, and a system can modulate electrical stimulation using the characteristic value as feedback.

When in different posture states (e.g., sitting as compared to laying in the supine position), the different distances between the electrodes and target tissue cause the patient to have different levels of sensitivity to changes in stimulation parameters that define electrical stimulation. In this manner, a growth curve of the ECAP signal (e.g., the relationship between the characteristic value of the ECAP and amplitude of the stimulation pulse) can depend on at least in part on a posture state of the patient. In one examples, the closer the distance between the electrodes and the target tissue, the greater the sensitivity and slope of the growth curve. As described herein, a system may use detected posture state of the patient to inform how the system uses the ECAP signal in a control policy that defines changes to stimulation parameter values for subsequent pulses, such as a frequency, an amplitude, a pulse width, and a pulse shape. Generally, informed stimulation pulses may be configured to contribute to a therapeutic effect of the patient, but ECAP signals may not be detectable from these informed stimulation pulses. Therefore, control stimulation pulses having a pulse width shorter than the informed stimulation pulses may be delivered to the patient in order to detect elicited ECAP signals. The control stimulation pulses may or may not contribute to a therapeutic effect for the patient. In one example, the system may select a gain value associated with a detected posture state for adjusting a parameter values for one or both of the control stimulation pulses and the informed stimulation pulses. The gain value may be associated with the respective growth curve of that detected posture state. In addition, or alternatively, the system may select a target ECAP characteristic value according to the detected posture state of the patient.

In one example, a system includes sensing circuitry configured to sense an evoked compound action potential (ECAP) signal elicited by a control stimulation pulse of a plurality of control stimulation pulses and processing circuitry configured to control delivery of a first informed stimulation pulse defined by at least a first value of an informed stimulation parameter, the informed stimulation pulse being one informed stimulation pulse of a plurality of informed stimulation pulse, control delivery of the control stimulation pulse to a patient, the control stimulation pulse defined by at least a first value of a control stimulation parameter, determine a characteristic value of the ECAP signal elicited from the control stimulation pulse, receive, from a sensor, a posture state signal representing a posture state of the patient, adjust, based on the characteristic value of the ECAP signal and the posture state signal, the first value of the informed stimulation parameter to a second value of the informed stimulation parameter; and control delivery of a second informed stimulation pulse of the plurality of informed stimulation pulses that is defined at least by the second value of the informed stimulation parameter.

In another example, a method includes controlling, by processing circuitry, delivery of a first informed stimulation pulse defined by at least a first value of an informed stimulation parameter, the informed stimulation pulse being one informed stimulation pulse of a plurality of informed stimulation pulse, controlling, by the processing circuitry, delivery of a control stimulation pulse of a plurality of control stimulation pulses to a patient, the control stimulation pulse defined by at least a first value of a control stimulation parameter, sensing, by sensing circuitry, an evoked compound action potential (ECAP) signal elicited by the control stimulation pulse, determining, by the processing circuitry, a characteristic value of the ECAP signal elicited from the control stimulation pulse, receiving, by the processing circuitry and from a sensor, a posture state signal representing a posture state of the patient, adjusting, by the processing circuitry and based on the characteristic value of the ECAP signal and the posture state signal, the first value of the informed stimulation parameter to a second value of the informed stimulation parameter, and controlling, by the processing circuitry, delivery of a second informed stimulation pulse of the plurality of informed stimulation pulses that is defined at least by the second value of the informed stimulation parameter.

In another example, a computer-readable storage medium including instructions that, when executed by processing circuitry, cause the processing circuitry to control delivery of a first informed stimulation pulse defined by at least a first value of an informed stimulation parameter, the informed stimulation pulse being one informed stimulation pulse of a plurality of informed stimulation pulse, control delivery of a control stimulation pulse of a plurality of control stimulation pulses to a patient, the control stimulation pulse defined by at least a first value of a control stimulation parameter, control sensing circuitry to sense an evoked compound action potential (ECAP) signal elicited by the control stimulation pulse, determine a characteristic value of the ECAP signal elicited from the control stimulation pulse, receive, from a sensor, a posture state signal representing a posture state of the patient, adjust, based on the characteristic value of the ECAP signal and the posture state signal, the first value of the informed stimulation parameter to a second value of the informed stimulation parameter, and control delivery of a second informed stimulation pulse of the plurality of informed stimulation pulses that is defined at least by the second value of the informed stimulation parameter The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages of the techniques will be apparent from the description and drawings, and from the claims.

BRIEF DESCRIPTION OF DRAWINGS

Like reference characters denote like elements throughout the description and figures.

DETAILED DESCRIPTION

Figure 1:
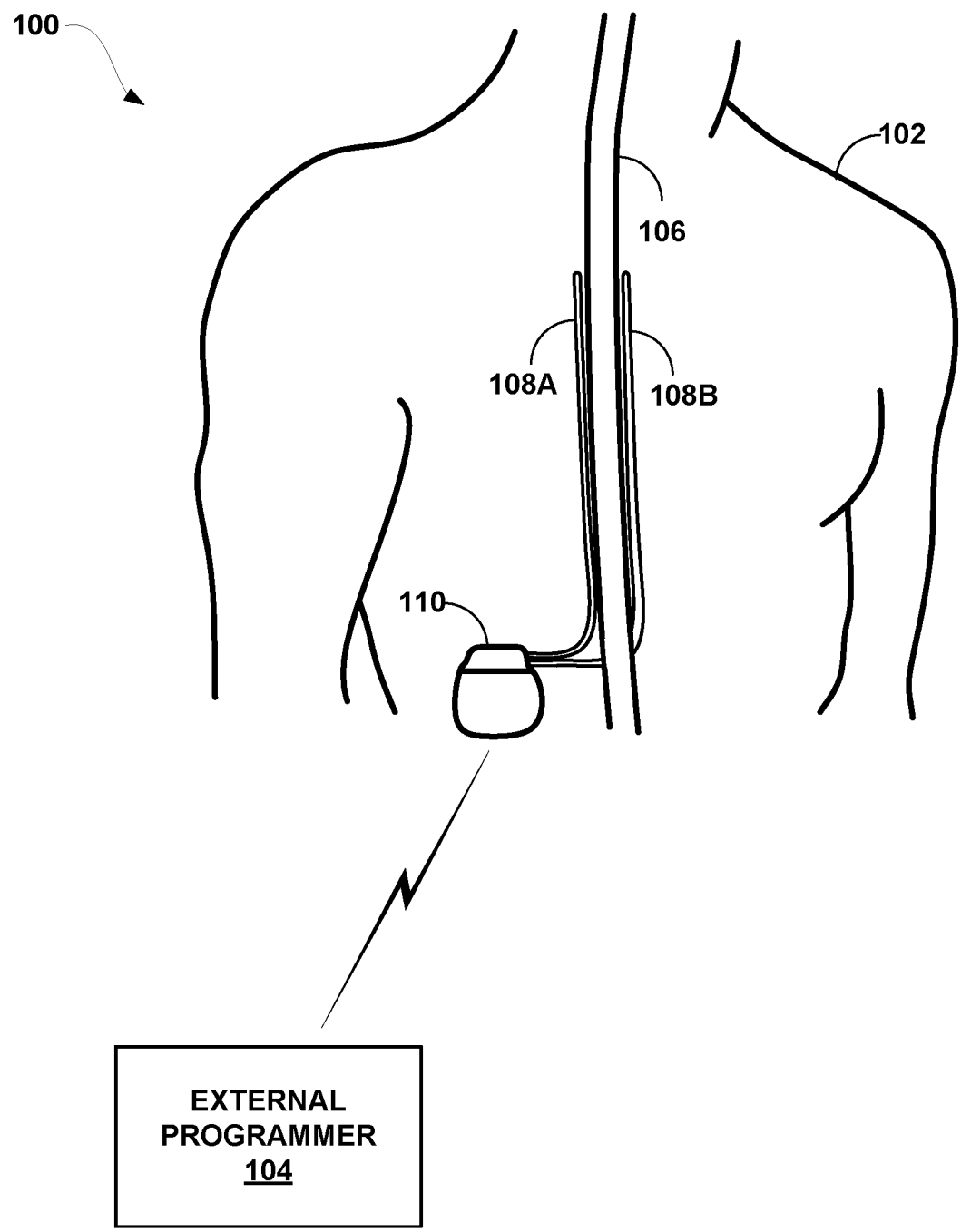
FIG. 1 is a conceptual diagram illustrating an example system that includes a medical device programmer and an IMD according to the techniques of the disclosure.

The disclosure describes examples of medical devices, systems, and techniques for adjusting electrical stimulation delivered to a patient based on a posture state of the patient and one or more characteristics of ECAP signals. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. However, as the patient moves, the distance between the electrodes and the target tissues changes. Since neural recruitment at the nerves is a function of stimulation intensity (e.g., amplitude and/or pulse frequency) and distance between the target tissue and the electrodes, movement of the electrode closer to the target tissue may result in increased neural recruitment (e.g., possible painful sensations or adverse motor function), and movement of the electrode further from the target tissue may result in decreased efficacy of the therapy for the patient. Certain patient postures (which may or may not include patient activity) may be representative of respective distances (or changes in distance) between electrodes and nerves and thus be an informative feedback variable for modulating stimulation therapy.

In some examples, a patient may experience discomfort or pain caused by transient patient conditions, which is referred to herein as transient overstimulation. The electrodes can move closer to the target tissue for a number of reasons including coughing, sneezing, laughing, valsalva maneuvers, leg lifting, cervical motions, deep breathing, or another transient patient movement. If a system is delivering stimulation during these movements, the patient may perceive the stimulation as stronger (and possibly uncomfortable) due to the decreased distance between electrodes and target tissue in a short amount of time. Although a patient may anticipate such movements and preemptively reduce stimulation intensity in an attempt to avoid these uncomfortable sensations, these patient actions interfere with normal activities and may not be sufficient to avoid uncomfortable stimulation at all times.

ECAPs are a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude, or area under a curve). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased.

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation). However, if the patient changes posture or otherwise engages in physical activity, the distance between the electrodes and the nerve changes as well.

This change in distance can cause loss of effective therapy and/or side effects if the parameter values that define stimulation are not adjusted to compensate for the change in distance. Moreover, the different distance between electrodes and the target nerve (e.g., caused by a shift from one posture state to another) may also result in different sensitivities to stimulation intensity (e.g., smaller distances may result in greater sensitivities to changes in stimulation intensity). If a system does not adjust the control policy for these changes, adjustments to stimulation parameter values may not be sufficient to maintain effective therapy or may provide stimulation that is too strong at that posture state. Therefore, it may be beneficial to maintain effective therapy by the system adjusting how stimulation intensity is changed within a given posture state and/or changing target ECAP characteristic values when a posture state of the patient has changed.

As described herein, systems, devices, and techniques provide solutions to one or more of the above-referenced problems by adjusting electrical stimulation therapy delivered to a patient based on a posture state of the patient and one or more characteristics of ECAP signals. As discussed above, when a patient moves, the distance between implanted electrodes and target nerves changes. For example, electrodes implanted along the spinal column move to a position closer to the spinal cord when a subject lies in a supine posture state as compared to a position farther from the spinal cord when the subject assumes a standing posture state. Since the posture state can affect the distance between the electrodes and target nerve, the system may detect or otherwise obtain the current posture state of the patient and adjust one or more aspects of the control policy employed by the system to modulate stimulation therapy in response to detected ECAP signals. A posture state may refer to a patient posture, an activity level, or a combination of patient posture and activity level. In some examples, the system may select a therapy program or set of stimulation parameter values according to the detected posture state of the patient.

The system may store or otherwise obtain gain values, growth curves, target ECAP characteristic values, or other factors that affect modulation of stimulation associated with respective posture states. Electrical stimulation may be delivered to a patient by the medical device in a train of stimulation pulses, and parameters that define the stimulation pulses may include pulse amplitude (current and/or voltage), pulse frequency, pulse width, pulse shape, and/or electrode combination. The system may alter, adjust, change, or otherwise modulate one or more parameters of the stimulation pulses over time in order to maintain a desired level of stimulation efficacy for the patient.

Nerve impulses detectable as the ECAP signal travel quickly along the nerve fiber after the delivered stimulation pulse first depolarizes the nerve. If the stimulation pulse that elicits the ECAP signal is delivered by first electrodes has a pulse width that is too long, different electrodes configured to sense the ECAP will sense the stimulation pulse itself as an artifact that obscures the lower amplitude ECAP signal. Although sensing electrodes could be positioned farther away from where the stimulation pulse is delivered to avoid this artifact, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs elicited by certain stimulation pulses having relatively long pulse widths that interfere with detection of ECAP signals (e.g., stimulation pulses that may be configured to provide a therapeutic effect for the patient).

To avoid this ECAP detection problem with some stimulation pulses, a medical device may be configured to deliver a plurality of control pulses and a plurality of informed pulses in some examples. Informed pulses may be configured to contribute to a therapeutic effect for the patient, but the informed pulses may have a stimulation parameter, such as a pulse width, that overlaps with the ECAP signal and prevents the system from detecting the ECAP signal or otherwise using the ECAP signal for feedback for modulating parameter values of the informed pulses. The plurality of control pulses, on the other hand, may be configured to elicit detectable ECAP signals. For example, the control pulses may have a pulse width that is short enough to avoid interfering with the ECAP signal detection. The control pulses may or may not contribute to a therapeutic effect for the patient. In this manner, the system may be configured to adjust one or more parameters that define the informed pulses based on the detectable ECAP signals elicited by one or more control pulses.

In one example described herein, a medical device can deliver a plurality of informed pulses to provide a therapy to the patient and a plurality of control pulses. At least some of the control pulses may elicit a detectable ECAP signal without the primary purpose of providing a therapy to the patient. The control pulses may be interleaved with the delivery of the informed pulses. For example, the medical device may alternate the delivery of informed pulses with control pulses such that a control pulse is delivered, and an ECAP signal is sensed, between consecutive informed pulses. In some examples, multiple control pulses are delivered, and respective ECAP signals sensed, between the delivery of consecutive informed pulses. In some examples, multiple informed pulses will be delivered between consecutive control pulses. In any case, the informed pulses may be delivered according to a predetermined pulse frequency selected so that the informed pulses can produce a therapeutic result for the patient. One or more control pulses are then delivered, and the respective ECAP signals sensed, within one or more time windows between consecutive informed pulses delivered according to the predetermined pulse frequency. In this manner, a medical device can administer informed pulses from the medical device uninterrupted while ECAPs are sensed from control pulses delivered during times at which the informed pulses are not being delivered. In other examples described herein, ECAPs are sensed by the medical device in response to the informed pulses delivered by the medical device, and control pulses are not used to elicit ECAPs.

The system may monitor one or more characteristic values that represent detected ECAP signals and adjust a stimulation parameter value in an attempt to achieve a target ECAP characteristic value. The system may adjust an informed parameter that at least partially defines subsequent informed pulses and may adjust a control parameter that at least partially defines subsequent control pulses. When adjusting the informed parameter value and/or the control parameter value in response to determining that the sensed characteristic value of the ECAP signal is below or above the target ECAP characteristic value, the system may employ a gain value that represents the magnitude, or rate, of change applied to a stimulation parameter in order to achieve the target ECAP characteristic value. The gain value may be the same or different for informed pulses and control pulses. In some examples, the system may apply a scaling factor or otherwise adjust the gain value so that it is appropriate for informed pulses and control pulses that may have different amplitudes or other parameters. For example, if the control pulse has a higher amplitude value than the informed pulse, the system may effectively reduce the gain value, or reduce the effect of the gain value, on the change to the informed pulse amplitude because the lower amplitude value of the informed pulse may not need to be changes as much as the control pulse amplitude. The system can thus increase or decrease a stimulation parameter according to the gain value in order to maintain the target ECAP characteristic value.

In some examples, the gain value may be a multiplier applied to a difference between a target ECAP characteristic value and a detected ECAP characteristic value. If the gain value is constant, the result is a stimulation parameter value that changes linearly. For example, the system may select one gain value for any detected ECAP characteristic value that is less than the target ECAP characteristic value, and the system may select a different gain value for any detected ECAP characteristic value that is greater than the target ECAP characteristic value. In other examples, the gain value may be calculated using a function that may be linear or non-linear. Put another way, for a given input or set of inputs (e.g., the detected ECAP characteristic value and/or posture state may be an input that affects the calculated gain value) the system may calculate different gain values for increasing stimulation intensity and/or decreasing stimulation intensity.

In one example, the system may determine a gain value that changes for different sensed ECAP characteristic values or different differences between the sensed ECAP characteristic value and a target ECAP characteristic value. A changing gain value (via a linear or non-linear function) would result in a non-linear function that determines the adjusted stimulation parameter (e.g., the output of the non-linear function). For example, the system may adjust the stimulation parameter value exponentially or logarithmically according to the difference between the sensed ECAP characteristic value and the threshold ECAP amplitude. In one example, the gain value is calculated by multiplying the difference between the sensed ECAP characteristic value and the threshold ECAP amplitude to a multiplier (e.g., a linear function) such that the gain value changes according to that difference between the sensed ECAP characteristic value and the threshold ECAP amplitude. In some examples, the gain value may represent a value selected from a table that stores gain values for respective difference values between the sensed ECAP characteristic value and the threshold ECAP amplitude. The table may result in a linear or non-linear function for determining the next stimulation parameter value.

For example, a larger gain value will cause the system to make a larger adjustment to a stimulation parameter (e.g., informed parameter or control parameter) for the same stimulation pulse than the adjustment resulting from a smaller gain value. For a non-linear function this comparison in gain value can be made relative to the same value for the difference between the sensed ECAP characteristic value and the threshold ECAP amplitude (e.g., the value difference representing an input value to the gain function). Thus, for a given input value of the gain function (or set of input values) the corresponding gain value (or set of gain values) is changed. For ease of discussion, various examples discuss the change in gain value relative to a linear function. It is understood that a non-linear function may also be used in such embodiments, where the relative change in gain value is thereby relative to the same value for the difference between the sensed ECAP characteristic value and the threshold ECAP amplitude.

Without different gain values for different posture states, a system may respond too slowly or too quickly with adjustments to stimulation parameter values. If the gain value is too large for the posture state, the system may overcorrect a stimulation parameter value (e.g., cause an uncomfortable sensation or reduce therapy efficacy). If the gain value is too small for the posture state, the system may require many iterations of adjustments to the stimulation parameter before the appropriate stimulation intensity is provided (e.g., also causing a prolonged uncomfortable sensation or a prolonged period of ineffective therapy). Generally, posture states associated with farther distances between the electrodes and target nerve may generally have larger gain values than posture states associated with closer distances between the electrodes and target nerve. In this manner, smaller gain values may be associated with smaller distances between electrodes and the target nerve (e.g., posture states more sensitive to changes in stimulation intensity such as a supine posture state). Conversely, larger gain values may be associated with larger distances between electrodes and the target nerve (e.g., posture states less sensitive to changes in stimulation intensity such as a prone posture state). A gain value may be inversely proportional to a growth curve for a particular posture state, wherein the growth curve may be a best fit curve or line of ECAP characteristic values (e.g., voltage amplitude) for given stimulation parameter values (e.g., a current amplitude of the respective pulses that elicited respective ECAP signals). In some examples, the target ECAP characteristic value may be the same for some or all posture states, but the target ECAP characteristic value may be different between posture states in other examples. In this manner, the system may select the target ECAP characteristic value associated with the detected posture state.

In another type of control policy (e.g., type of closed-loop feedback scheme), the system may employ a threshold ECAP characteristic value instead of a target ECAP characteristic value. The system may monitor characteristic values for sensed ECAP signals and reduce one or more stimulation parameter values (e.g., informed parameter values and/or control parameter values) from a predetermined value only in response to the characteristic value exceeding the threshold ECAP characteristic value. In other words, the system may be configured to attempt to keep characteristic values of sensed ECAP signals below the threshold ECAP characteristic value and only increase the stimulation parameter back up to the predetermined value in response to the characteristic value dropping back below the threshold ECAP characteristic value. In some examples, the system may select the gain value used for adjusting the stimulation parameter according to the current posture state of the patient. In addition, or alternatively, the system may select the threshold ECAP characteristic value according to the detected posture state of the patient.

In some examples, stimulation parameter values may be predetermined and/or automatically adjusted by the system based on characteristic values of ECAP signals, posture states, and other types of feedback. An external programmer for an IMD may provide a variety of features to support association of stimulation parameter values and/or characteristic values of ECAP signals with different posture states.

As one example, the programmer may receive user input indicating the posture state that the patient is occupying and associated ECAP signals, and/or corresponding characteristic values, with that posture state. As another example, a patient may indicate a value for a previously undefined stimulation parameter value for a defined posture state while the patient is in the posture state or transitioning to the posture state. The indicated value may be defined for the posture state. As another example, a user may link multiple posture states and select a set of stimulation parameter values for delivery of therapy for each of the linked posture states. In this manner, it may not be necessary to specify separate sets of stimulation parameter values for each individual posture state.

In some examples, a medical device, e.g., an implantable medical device (IMD), that delivers electrical stimulation may also employ a posture state detector (e.g., one or more sensors) that detects the patient posture state. In other examples, the IMD may receive data from one or more a separate devices that sense the posture state of the patient. The IMD may then adjust one or more stimulation parameters in response to different posture states as indicated by the posture state detector.

A user may define stimulation parameter values (e.g., informed parameter values for informed pulses and/or control parameter values for control pulses) for delivery of therapy to a patient and associate the stimulation parameter values with multiple posture states based on user input, e.g., simultaneously. As another example, upon storing a set of pre-established posture state definitions for delivery of posture state-responsive therapy, a device may permit a patient to submit a request via a patient programmer to update the set of pre-established posture state definitions. For example, programmer may be configured to receive user input changing the definitions of one or more posture states. In addition, a posture state definition may be modified based on user therapy adjustments and/or posture state information. In some cases, the posture state may be expanded and split. In other cases, the posture state may be reduced in size based on posture state information. Hence, using one or more of the features described in this disclosure, stimulation parameter values may be flexibly, conveniently, and efficiently specified for various posture states, including predetermined posture states and patient-created posture states.

Informed pulses and control pulses are generally described herein as different stimulation pulses reflective of different types of electrical stimulation. However, the different types of electrical stimulation, and their respective pulses, may be described with different attributes. For example, a first type of electrical stimulation may include first pulses (such as informed pulses) configured to primarily contribute to a therapy for a patient. The first pulses of this first type of electrical stimulation may also have one or more characteristics (e.g., a pulse width) that prevent or reduce the ability of the system to detect ECAP signals elicited from the first pulses of the first type of electrical stimulation because an artifact representative of the first pulses themselves overlaps with and obscures at least a portion of the respective elicited ECAP signal. A second type of electrical stimulation may include second pulses (such as control pulses) defined by one or more parameter values selected to elicit ECAP signals that are sensed and detectable by the system. The second pulses may thus be referred to as "sense pulses" or "test pulses" since the second pulses are configured to elicit a detectable ECAP signal. For example, the second pulses of the second type of electrical stimulation may improve the detectability of the ECAP signal such as not to generate an artifact that obscures the ECAP signals or otherwise prevents or reduces the ability of the system to detect the ECAP signal from each of the second pulses. In addition, the second pulses may be defined by parameter values selected to elicit an ECAP signal that is used to at least modify one or more parameter values of the first pulses of the first type of electrical stimulation. The first pulses may thus differ from the second pulses by at least one parameter (e.g., current and/or voltage amplitude, pulse width, and/or frequency). The first pulses may be at least partially interleaved with at least some of the second pulses. For example, the system may alternate delivery of one first pulse with delivery of one second pulse. In another example, the number of first pulses may differ from the number of second pulses by a ratio or percentage. The ratio could be 1:1 when the first and second pulses are fully interleaved. The ratio could be 10:1 first pulses to second pulses in examples in which the second pulses are delivered less frequently than the first pulses. In other examples, the ratio could be 1:4 first pulses to second pulses when the second pulses, and respective sensed ECAP signals) occur more frequently than the first pulses. The second pulses may or may not contribute to a therapy and/or sensation perceived by the patient, but the primary purpose of the second pulses is to elicit respective ECAP signals that are detectable by the system separate from any sensed artifacts representative of the second pulses themselves.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating example system 100 that includes implantable medical device (IMD) 110 to deliver electrical stimulation therapy to patient 102. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 108A and 108B, and external programmer 104 shown in conjunction with a patient 102, who is ordinarily a human patient. In the example of FIG. 1, IMD 110 is an implantable electrical stimulator that is configured to generate and deliver electrical stimulation therapy to patient 102 via one or more electrodes of electrodes of leads 108A and/or 108B (collectively, "leads 108"), e.g., for relief of chronic pain or other symptoms. In other examples, IMD 110 may be coupled to a single lead carrying multiple electrodes or more than two leads each carrying multiple electrodes. In some examples, the stimulation signals, or pulses (e.g., control pulses), may be configured to elicit detectable ECAP signals that IMD 110 may use to determine the posture state occupied by patient 102 and/or determine how to adjust one or more parameters that define stimulation therapy. IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes (not shown) of implantable leads 108. In the example of FIG. 1, leads 108 carry electrodes that are placed adjacent to the target tissue of spinal cord 106. One or more of the electrodes may be disposed at a distal tip of a lead 108 and/or at other positions at intermediate points along the lead. Leads 108 may be implanted and coupled to IMD 110. The electrodes may transfer electrical stimulation generated by an electrical stimulation generator in IMD 110 to tissue of patient 102. Although leads 108 may each be a single lead, lead 108 may include a lead extension or other segments that may aid in implantation or positioning of lead 108. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 108 will be described for purposes of illustration.

The deployment of electrodes via leads 108 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 108 are linear leads having 8 ring electrodes along the axial length of the lead. In another example, the electrodes are segmented rings arranged in a linear fashion along the axial length of the lead and at the periphery of the lead.

The stimulation parameter set of a stimulation program that defines the stimulation pulses of electrical stimulation therapy by IMD 110 through the electrodes of leads 108 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input. Informed pulses may be defined by a set of informed stimulation parameter values and control pulses may be defined by a set of control stimulation parameter values.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, lead 108 includes one or more sensors configured to allow IMD 110 to monitor one or more parameters of patient 102, such as patient activity, pressure, temperature, or other characteristics. The one or more sensors may be provided in addition to, or in place of, therapy delivery by lead 108.

IMD 110 is generally configured to deliver electrical stimulation therapy (e.g., informed pulses and/or control pulses) to patient 102 via selected combinations of electrodes carried by one or both of leads 108, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 106, such as within an intrathecal space or epidural space of spinal cord 106, or, in some examples, adjacent nerves that branch off spinal cord 106. Leads 108 may be introduced into spinal cord 106 in via any suitable region, such as the thoracic, cervical or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results.

IMD 110 is configured to generate and deliver electrical stimulation therapy to a target stimulation site within patient 102 via the electrodes of leads 108 to patient 102 according to one or more therapy stimulation programs. A therapy stimulation program may generally define informed pulses, but may also define control pulses if the control pulses also contribute to a therapeutic effect). A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

A user, such as a clinician or patient 102, may interact with a user interface of an external programmer 104 to program IMD 110. Programming of IMD 110 may refer generally to the generation and transfer of commands, programs, or other information to control the operation of IMD 110. In this manner, IMD 110 may receive the transferred commands and programs from external programmer 104 to control stimulation, such as stimulation pulses that provide electrical stimulation therapy. For example, external programmer 104 may transmit therapy stimulation programs, stimulation parameter adjustments, therapy stimulation program selections, posture states, user input, or other information to control the operation of IMD 110, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 104 may include, or be part of, an external charging device that recharges a power source of IMD 110. In this manner, a user may program and charge IMD 110 using one device, or multiple devices.

As described herein, information may be transmitted between external programmer 104 and IMD 110. Therefore, IMD 110 and external programmer 104 may communicate via wireless communication using any techniques known in the art. Examples of communication techniques may include, for example, radiofrequency (RF) telemetry and inductive coupling, but other techniques are also contemplated. In some examples, external programmer 104 includes a communication head that may be placed proximate to the patient's body near the IMD 110 implant site to improve the quality or security of communication between IMD 110 and external programmer 104. Communication between external programmer 104 and IMD 110 may occur during power transmission or separate from power transmission.

In some examples, IMD 110, in response to commands from external programmer 104, delivers electrical stimulation therapy (e.g., informed pulses and/or control pulses) according to a plurality of therapy stimulation programs to a target tissue site of the spinal cord 106 of patient 102 via electrodes (not depicted) on leads 108. In some examples, IMD 110 modifies therapy stimulation programs as therapy needs of patient 102 evolve over time. For example, the modification of the therapy stimulation programs may cause the adjustment of at least one parameter of the plurality of stimulation pulses. When patient 102 receives the same therapy for an extended period, the efficacy of the therapy may be reduced. In some cases, parameters of the plurality of stimulation pulses may be automatically updated.

As described herein, IMD 110 may be configured to detect ECAP signals which are representative of the number of nerve fibers activated by a delivered stimulation signal (e.g., a control pulse). Since the distance between electrodes and the target nerve changes for different posture states (e.g., a static posture and/or activity component), a characteristic value of one or more ECAP signals can be indicative of the posture state currently occupied when the one or more ECAP signals were detected by IMD 110. In one example, IMD 110 may deliver a plurality of control pulses defined by different parameter values and detect the respective ECAP signal elicited by each pulse. IMD 110 may determine a relationship between characteristic values from each ECAP signal and the different parameter values of the control pulses, and this relationship may be different for each different posture state. In one example, the relationship may be a curve of the characteristic values of the ECAP (e.g., an amplitude of the ECAP signal) vs. values of a stimulation parameter (e.g., the current amplitude of the respective control pulses) that elicited each ECAP signal from which the characteristic values were derived. Each posture state may have a respective curve that varies in slope and/or intercept. In some examples, a gain value may be determined from the slope of the growth curve, wherein the gain value may be inversely proportional to the slope.

In this disclosure, efficacy of electrical stimulation therapy may be indicated by one or more characteristics (e.g. an amplitude of or between one or more peaks or an area under the curve of one or more peaks) of an action potential that is evoked by a control pulse delivered by IMD 110 (i.e., a characteristic value of the ECAP signal). Electrical stimulation therapy delivery by leads 108 of IMD 110 may cause neurons within the target tissue to evoke a compound action potential that travels up and down the target tissue, eventually arriving at sensing electrodes of IMD 110. Furthermore, stimulation may also elicit at least one ECAP signal, and ECAPs responsive to stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the control pulse at the beginning and/or end of each control pulse or each phase within the pulse. For example, a very high slew rate indicates a steep or even near vertical edge of the pulse, and a low slew rate indicates a longer ramp up (or ramp down) in the amplitude of the control pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control pulses.

Some example techniques for adjusting stimulation parameter values for stimulation pulses (e.g., informed pulses and/or control pulses that may or may not contribute to therapy for the patient) are based on comparing the value of a characteristic of a measured ECAP signal to a target ECAP characteristic value. In response to delivering a control pulse defined by a set of stimulation parameter values, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sense circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of patient 102. Examples of the one or more sensors include one or more sensors configured to measure a compound action potential of patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, or a sensor configured to detect a respiratory function of patient 102. However, in other examples, external programmer 104 receives a signal indicating a compound action potential in the target tissue of patient 102 and transmits a notification to IMD 110.

In the example of FIG. 1, IMD 110 is described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation therapy based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more stimulation parameter that defines the electrical stimulation informed pulses and, in some examples, control pulses, delivered to patient 102.

In some examples, the system changes the target ECAP characteristic value and/or growth rate(s) over a period of time, such as according to a change to a stimulation threshold (e.g., a perception threshold or detection threshold specific for the patient). The system may be programmed to change the target ECAP characteristic in order to adjust the intensity of informed pulses to provide varying sensations to the patient (e.g., increase or decrease the volume of neural activation). Although the system may change the target ECAP characteristic value, received ECAP signals may still be used by the system to adjust one or more parameter values of the informed pulses and/or control pulses in order to meet the target ECAP characteristic value.

One or more devices within system 100, such as IMD 110 and/or external programmer 104, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses (e.g., control pulses) having different amplitude values and control the sensing circuitry to detect, after delivery of each electrical stimulation pulse of the plurality of electrical stimulation pulses, a respective ECAP signal of the plurality of ECAP signals. The processing circuitry of IMD 110 may then determine, based on the plurality of ECAP signals, a posture state of the patient.

As described herein, IMD 110 may modulate or adjust one or more stimulation parameters that at least partially define electrical stimulation based on a detected posture state of the patient 102. IMD 110 may use the detected posture state to determine how to employ ECAP signals in a closed-loop feedback system for adjusting stimulation parameters that define informed pulses and/or control pulses. In one example, IMD 110 includes stimulation generation circuitry configured to generate and deliver electrical stimulation to patient 102 according one or more sets of stimulation parameters (e.g., informed parameters and/or control parameters) that at least partially define the respective informed pulses and/or control pulses of the electrical stimulation. Each set of stimulation parameters may include at least one of an amplitude, a pulse width, a pulse frequency, or a pulse shape.

IMD 110 may also include sensing circuitry configured to sense an ECAP signal elicited by delivered electrical stimulation, such as a control pulse. IMD 110 may also include processing circuitry configured to control delivery of an informed pulses to patient 102 according to a first value of an informed stimulation parameter and determine a characteristic value of the ECAP signal detected from the control pulse. IMD 110 may also receive, from a sensor, a posture state signal representing a posture state of the patient. In some examples, IMD 110 may then determine, based on the posture state signal, a gain value for the stimulation parameter and adjust, based on the characteristic value of the ECAP signal and the gain value, the first value of the informed stimulation parameter to a second value of the informed stimulation parameter. In other examples, IMD 110 may additionally, or alternatively, adjust a target ECAP characteristic value or a threshold ECAP characteristic value based on the posture state signal. IMD 110 may then control subsequent delivery of one or more informed stimulation pulses according to the second value of the informed stimulation parameter. In this manner, an informed parameter value that defines the next informed pulse was "informed" by the ECAP signal elicited by a control pulse.

In some examples, the processing circuitry of IMD 110 may be configured to adjust the first value of the informed parameter to the second value of the informed parameter by one of increasing or decreasing the informed parameter of the informed pulses based on a growth curve associated with the posture state of the patient. In addition, the processing circuitry may be configured to adjust a control parameter value for subsequent control pulses based on the growth curve. As discussed herein, the growth curve may represent a relationship between one or more parameters of delivered control pulses and a characteristic of ECAP signals. For example, the characteristic may be an amplitude of the ECAP signals (e.g., an amplitude between an N1 peak and a P2 peak of the ECAP signal), an area under one or more peaks of the ECAP signal, or some other metric indicative of the nerve activation that resulted in the ECAP signal. In some examples, the gain value may be inversely proportional to a slope of the growth curve.

When IMD 110 is configured to modulate stimulation pulses in order to maintain consistent nerve activation, such as increasing and decreasing a stimulation parameter to maintain a target ECAP characteristic value, IMD 110 may perform an example process. For example, IMD 110 may monitor an amplitude that is the characteristic value of the detected ECAP signal. IMD 110 may adjust the first value to the second value of the informed stimulation parameter by subtracting the amplitude from a target ECAP amplitude value for the patient to generate a differential amplitude. The differential amplitude is the difference between the detected amplitude from the ECAP signal and the target ECAP amplitude value. IMD 110 may then multiply the differential amplitude by the gain value that at least partially defines the control pulses to generate a differential value. The gain value may be a multiplier or fraction selected based on the detected posture state. A larger gain value may be associated with posture states at which the distance between electrodes and the target nerve is larger because the distance causes less sensitivity for changes in stimulation pulse intensity. IMD 110 may then add the differential value to a previous amplitude value (e.g., the amplitude value of the last control pulse that was delivered and elicited the ECAP signal) to generate the second value that at least partially defines the next control pulse to be delivered to patient 102. IMD 110 may then multiple the differential value by a scaling factor to generate an informed differential value representing how much the amplitude of the informed pulses needs to change. The scaling factor may be greater than one when the informed pulse amplitude is greater than the control pulse amplitude, and conversely, the scaling factor may be less than one when the informed pulse amplitude is less than the control pulse amplitude. IMD 110 can then add the informed differential value to the previous amplitude value of the informed pulses to generate a second value of the informed pulses for subsequent delivery to the patient.

In other examples, IMD 110 may not attempt to maintain consistent nerve activation by modulating stimulation pulses to achieve a target ECAP characteristic value. Instead, IMD 110 may monitor characteristic values of ECAP signals and only take action when the characteristic value exceeds a threshold ECAP characteristic value. Characteristic values exceeding the threshold ECAP characteristic values may be indicative of increased stimulation perception that may be above an uncomfortable threshold or pain threshold for the patient. Therefore, reducing stimulation pulse intensity when the characteristic value exceeds this level of stimulation may reduce the likelihood that patient 102 experiences any uncomfortable sensations that may occur as a result of posture state changes or any transient movement. For example, IMD 110 may be configured to compare the characteristic value of the ECAP signal to a threshold ECAP characteristic value and determine that the characteristic value of the ECAP signal is greater than the threshold ECAP characteristic value. Responsive to determining that the characteristic value of the ECAP signal is greater than the threshold ECAP characteristic value, IMD 110 may be configured to decrease the first value of the informed stimulation parameter to the second value of the informed stimulation parameter for subsequent informed pulses to be delivered. Similarly, IMD 110 may be configured to decrease the value of a control stimulation parameter that defines subsequent control pulses to be delivered.

IMD 110 may continue to decrease the informed stimulation parameter value and/or the control stimulation parameter value as long as the ECAP characteristic value continues to exceed the threshold ECAP characteristic value. Once, the informed and control stimulation parameters have been decreased, IMD 110 may attempt to increase the informed and control stimulation parameter values again back up to the predetermined first value intended for the informed stimulation pulses and/or control stimulation pulses. IMD 110 may be configured to determine a other characteristic values of subsequent ECAP signals elicited from control stimulation pulses delivered after sensing the first ECAP signal. In response to determining that another characteristic value of the subsequent ECAP signals decreases below the threshold ECAP characteristic value, IMD 110 may then increase the value of the informed and/or control stimulation parameter back up to a value limited to be less than or equal to the first value (e.g., back up to the predetermined value for the informed and/or control stimulation pulses that may be determined by a set of stimulation parameters or therapy program). In some examples, IMD 110 may iteratively increase the informed and/or control stimulation parameter values until the first value, or original value, is again reached after the characteristic values of the ECAP signal remain below the threshold ECAP characteristic value. IMD 110 may increase the informed and/or control stimulation parameter values at a slower rate than the informed and/or control stimulation parameter values are decreased, but, in other examples, IMD 110 may increase and decrease the informed and/or control stimulation parameters at the same rates.

The detected posture state may be one posture state of a plurality of posture states. In some examples, each posture state may be associated with a respective growth curve representing the relationship between the ECAP values and control stimulation parameter values when the patient occupies that particular posture state. In some examples, IMD 110 may select, based on the posture state signal, the gain value from a plurality of gain values associated with respective posture states. The gain value may represent at least one of an increment rate (e.g., how fast IMD 110 should increase the stimulation parameter value) or a decrement rate (e.g., how slow IMD 110 should decrease the stimulation parameter value) for the control stimulation parameter (or the informed stimulation parameter in some examples) that at least partially defines the control stimulation pulses. In other examples, the gain value may represent a particular magnitude that IMD 110 should increment or decrement a previous parameter value of control pulses and/or informed pulses each time IMD 110 increases or decrease the parameter value. This particular magnitude may effectively result in a rate of change at which IMD 110 can adjust a stimulation parameter value. In addition, or alternatively, IMD 110 may select the target ECAP characteristic value or the threshold ECAP characteristic value according to the detected posture state. A patient may or may not benefit from posture state specific target or threshold ECAP characteristic values.

IMD 110 may sense the posture state of patient 102 at predetermined intervals or during predetermined periods of time. In some examples, IMD 110 may sense the posture state in response to a trigger event, such as a patient-requested change in stimulation therapy, a sensed event representative of a patient condition such as pain, or any other triggers. In some examples, IMD 110 may modulate posture state sensing frequency based on whether or not posture state changes are detected. For example, IMD 110 may determine, from at least the signal representing the posture state of the patient, that the posture state of the patient has changed. Responsive to determining that the posture state has changed, IMD 110 may change at least one of an ECAP sensing frequency. IMD 110 may increase posture state sensing frequency when more posture state changes are expected and decrease posture state sensing frequency when fewer posture state changes are expected. Sensing frequency may refer to sensor sampling frequency and/or frequency at which processing circuitry analyzes data obtained from one or more sensors. In this manner, IMD 110 may modulate sensing frequency to conserve power consumption or otherwise reduce processing tasks.

As discussed herein, some example techniques for adjusting informed stimulation parameter values and/or control stimulation parameter values for electrical stimulation signals are based on comparing the value of a characteristic of a measured ECAP signal to a target ECAP characteristic value or using control parameter values at a determined target ECAP characteristic to inform adjustment of one or more control parameter values and/or informed parameter values to maintain the target ECAP according to known relationships between parameters. For example, during delivery of an electrical stimulation signal, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sensing circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of the patient 102. Examples of the one or more sensors include one or more sensors can measure a compound action potential of the patient 102, or a physiological effect indicative of a compound action potential. For example, to measure a physiological effect of a compound action potential, the one or more sensors may be an accelerometer, a pressure sensor, a bending sensor, a sensor can detect a posture of patient 102, or a sensor can detect a respiratory function of patient 102. However, in other examples, external programmer 104 receives a signal indicating a compound action potential in the target tissue of patient 102 and transmits a notification to IMD 110.

In the example of FIG. 1, IMD 110 described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation signal based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more parameters that define the electrical stimulation signal.

In the example techniques described herein, the informed stimulation parameter values, control stimulation parameter values, growth curves, posture states, and the target ECAP characteristic values (e.g., values of the ECAP indicative of target stimulation intensity) may be initially set at the clinic but may be set and/or adjusted at home by patient 102. Once the target ECAP characteristic values are set, the example techniques allow for automatic adjustment of informed and/or control stimulation parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 102.

In some examples, the system may change the target ECAP characteristic value over a period of time (e.g., based on a sensed posture state or change in patient conditions). The system may be programmed to change the target ECAP characteristic in order to adjust the intensity of the informed pulses and/or control pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 104 (e.g., a user request to change the values stored in the memory of IMD 110). In other examples, the target ECAP characteristic value may be programed to steadily increase or steadily decrease to a baseline target ECAP characteristic value over a period of time. In other examples, external programmer 104 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more informed and/or control parameter values of the electrical stimulation signal in order to meet the target ECAP characteristic value.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples.

Figure 2:
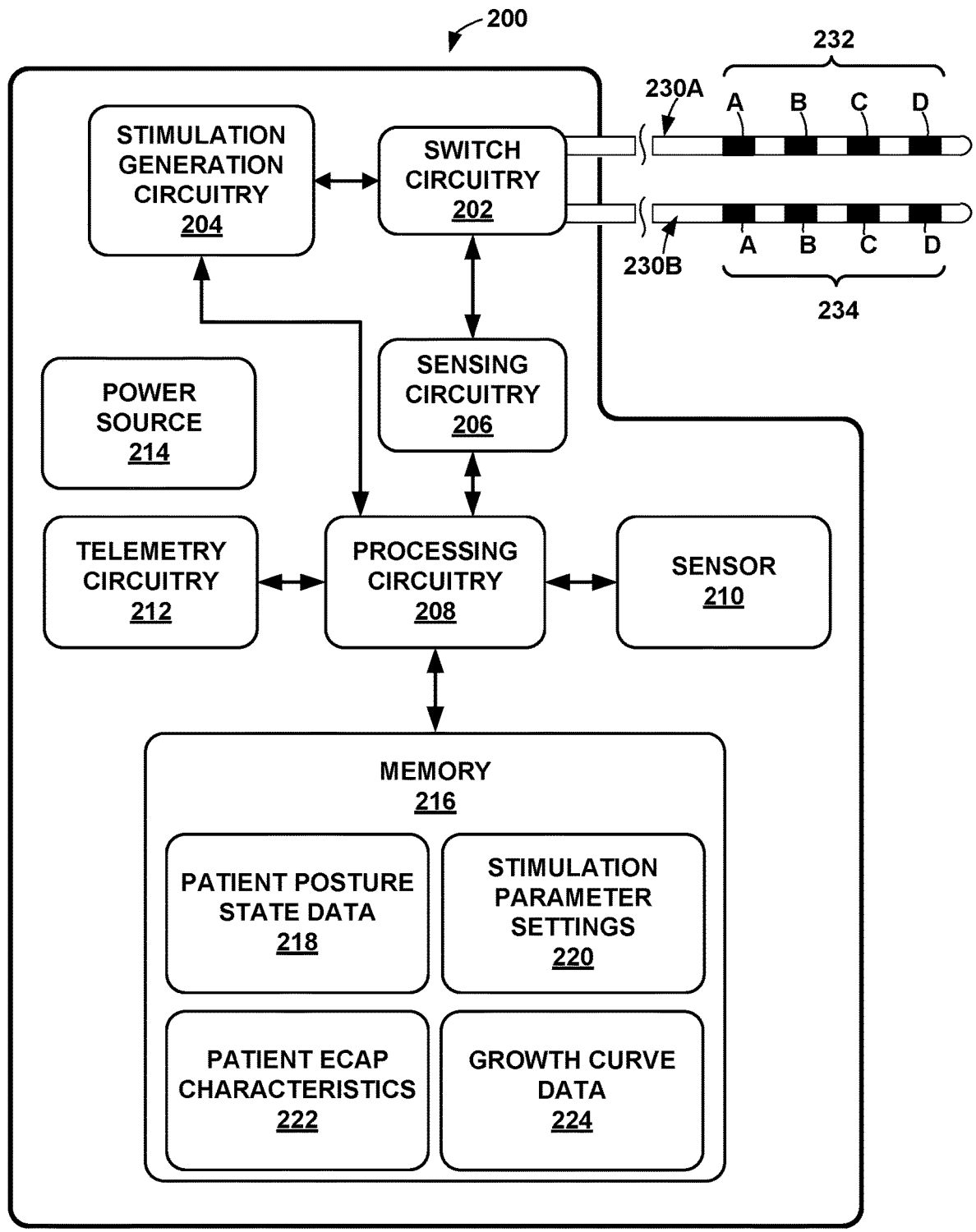
FIG. 2 is a block diagram of the example IMD of FIG. 1.

FIG. 2 is a block diagram of IMD 200. IMD 200 may be an example of IMD 110 of FIG. 1. In the example shown in FIG. 2, IMD 200 includes switch circuitry 202, stimulation generation circuitry 204, sensing circuitry 206, processing circuitry 208, sensor 210, telemetry circuitry 212, power source 214, and memory 216. Each of these circuits may be or include programmable or fixed function circuitry can perform the functions attributed to respective circuitry. For example, processing circuitry 208 may include fixed-function or programmable circuitry, stimulation generation circuitry 204 may include circuitry can generate electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 stores patient posture state data 218, which may include one or more patient postures, an activity level, or a combination of patient posture and activity level. A set of pre-established posture state definitions for a patient may be stored in patient posture state data 218. A posture state definition may be modified based on user therapy adjustments and/or posture state information. In some cases, the posture state may be expanded and split, or instead, may be reduced in size based on posture state information. The posture state definitions can be automatically updated or updated by a patient, including creating new posture states. Posture states may include, for example, a supine posture, a prone posture, a lying left and/or lying right, a sitting posture, a reclining posture, a standing posture, and/or activities such as running or riding in an automobile.

Memory 216 may store stimulation parameter settings 220 within memory 216 or separate areas within memory 216. Each stored stimulation parameter setting 220 defines values for one or more sets of electrical stimulation parameters (e.g., an informed stimulation parameter set and a control stimulation parameter set), such as pulse amplitude, pulse width, pulse frequency, electrode combination, pulse burst rate, pulse burst duration, and/or waveform shape. Stimulation parameter settings 220 may also include additional information such as instructions regarding delivery of electrical stimulation signals based on stimulation parameter relationship data, which can include relationships between two or more stimulation parameters based upon data from electrical stimulation signals delivered to patient 102 or data transmitted from external programmer 104. The stimulation parameter relationship data may include measurable aspects associated with stimulation, such as an ECAP characteristic value. Stimulation parameter settings 220, or another portion of memory 216, may include instructions on how processing circuitry 208 can modulate informed stimulation parameters and/or control stimulation parameters based on the detected posture state and/or at least one of a target ECAP characteristic value or a threshold ECAP characteristic value, as described herein.

Memory 216 also stores patient ECAP characteristics 222 which may include target ECAP characteristics and/or threshold ECAP characteristic values determined for the patient and/or a history of measured ECAP characteristic values for the patient. Memory 216 may also store growth curve data 224 in separate areas from or as part of patient stimulation parameter settings. Instead of, or in addition to growth curve data 224, memory 216 may include gain values that processing circuitry 208 may use to modulate informed and/or control stimulation pulses as described herein. In other examples, growth curve data 224 may include information regarding relationships between ECAP characteristics and control stimulation parameters for one or more posture states.

Accordingly, in some examples, stimulation generation circuitry 204 generates electrical stimulation signals (e.g., informed pulses and control pulses) in accordance with the electrical stimulation parameters noted above. Other ranges of stimulation parameter values may also be useful and may depend on the target stimulation site within patient 102. While stimulation pulses are described, stimulation signals may be of any form, such as continuous-time signals (e.g., sine waves) or the like. Switch circuitry 202 may include one or more switch arrays, one or more multiplexers, one or more switches (e.g., a switch matrix or other collection of switches), or other electrical circuitry configured to direct stimulation signals from stimulation generation circuitry 204 to one or more of electrodes 232, 234, or directed sensed signals from one or more of electrodes 232, 234 to sensing circuitry 206. In other examples, stimulation generation circuitry 204 and/or sensing circuitry 206 may include sensing circuitry to direct signals to and/or from one or more of electrodes 232, 234, which may or may not also include switch circuitry 202.

Sensing circuitry 206 may be configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver control stimulation pulses and/or informed stimulation pulses. Alternatively, in other cases, the particular combination of electrodes used for sensing ECAPs includes at least one of the same electrodes as a set of electrodes used to deliver informed and/or control stimulation pulses to patient 102. Sensing circuitry 206 may provide signals to an analog-to-digital converter, for conversion into a digital signal for processing, analysis, storage, or output by processing circuitry 208.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry can provide the functions attributed to processing circuitry 208 herein may be embodied as firmware, hardware, software or any combination thereof. Processing circuitry 208 controls stimulation generation circuitry 204 to generate electrical stimulation signals according to stimulation parameter settings 220 stored in memory 216 to apply stimulation parameter values, such as pulse amplitude, pulse width, pulse frequency, and waveform shape of each of the electrical stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 208 also controls stimulation generation circuitry 204 to generate and apply the electrical stimulation signals to selected combinations of electrodes 232, 234. In some examples, stimulation generation circuitry 204 includes a switch circuit (instead of, or in addition to, switch circuitry 202) that may couple stimulation signals to selected conductors within leads 230, which, in turn, deliver the stimulation signals across selected electrodes 232, 234. Such a switch circuit may be a switch array, switch matrix, multiplexer, or any other type of switch circuitry can selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 204 does not include a switch circuit and switch circuitry 202 does not interface between stimulation generation circuitry 204 and electrodes 232, 234. In these examples, stimulation generation circuitry 204 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 204, e.g., via switch circuitry 202 and/or switch circuitry of the stimulation generation circuitry 204, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 204 and processing circuitry 208 in FIG. 2, in other examples, sensing circuitry 206 may be in a separate housing from IMD 200 and may communicate with processing circuitry 208 via wired or wireless communication techniques.

In some examples, one or more of electrodes 232 and 234 may be suitable for sensing ECAPs. For instance, electrodes 232 and 234 may sense the voltage amplitude of a portion of the ECAP signals, where the sensed voltage amplitude is a characteristic the ECAP signal.

Memory 216 may be configured to store information within IMD 200 during operation. Memory 216 may include a computer-readable storage medium or computer-readable storage device. In some examples, memory 216 includes one or more of a short-term memory or a long-term memory. Memory 216 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 216 is used to store data indicative of instructions for execution by processing circuitry 208. As discussed herein, memory 216 can store patient posture state data 218, stimulation parameter settings 220, patient ECAP characteristics 222, and growth curve data 224.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity at least partially caused by a set of control stimulation parameter values. Sensor 210 may include one or more accelerometers, optical sensors, chemical sensors, temperature sensors, pressure sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210 may indicate a posture state (e.g., sleeping, awake, sitting, standing, or the like), and processing circuitry 208 may select target and/or threshold ECAP characteristic values according to the indicated posture state. In this manner, processing circuitry 208 may be configured to determine the currently occupied posture state of patient 102.

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as amplitude and electrode combination (e.g., for informed and/or control pulses), from the external programmer via telemetry circuitry 212. Updates to stimulation parameter settings 220 and input efficacy threshold settings 226 may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 delivers operating power to various components of IMD 200. Power source 214 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power consumption levels when needed to extend the operating time of power source 214. For example, power source 214 may switch to a lower pulse frequency based on the relationships of parameters that may provide similar ECAP characteristic values.

According to the techniques of the disclosure, stimulation generation circuitry 204 of IMD 200 receives, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAPs recorded at sensing circuitry 206 according to the following techniques.

Generally, the pulse width of informed pulses are greater than the pulse width of control pulses. This difference in pulse width may allow ECAPs elicited from the control pulses to be detectable by the system when the longer pulse widths of the informed pulses prevent elicited ECAPs, or at least some portion of the elicited ECAPs, from being detectable. In some examples, the plurality of informed stimulation pulses are defined by an informed pulse width greater than approximately 300 microseconds and less than approximately 1000 microseconds, while the plurality of control stimulation pulses are defined by a control pulse width less than approximately 300 microseconds. In one example, the plurality of informed pulses each have a pulse width of greater than approximately 300 μs and less than approximately 2000 μs (i.e., 2 milliseconds). In some examples, the informed pulse width is greater than approximately 300 μs and less than approximately 900 μs. In another example, the informed pulse width is greater than approximately 300 μs and less than approximately 500 μs. In one example, the informed pulses have a pulse width of approximately 450 μs and a pulse frequency of approximately 60 Hertz. Amplitude (current and/or voltage) for the pulses may be between approximately 0.5 mA (or volts) and approximately 10 mA (or volts), although amplitude may be lower or greater in other examples.

In one example, the predetermined pulse frequency of the plurality of informed pulses may be less than approximately 400 Hertz. In some examples, the predetermined pulse frequency of the plurality of pulses may be between approximately 50 Hertz and 70 Hertz. In one example, the predetermined pulse frequency of the plurality of pulses may be approximately 60 Hertz. However, the informed pulses may have frequencies greater than 400 Hertz or less than 50 Hertz in other examples. In addition, the informed pulses may be delivered in bursts of pulses, with interburst frequencies of the informed pulses being low enough such that a sensed ECAP elicited by a control pulse can still fit within the window between consecutive pulses delivered within the burst of pulses. In any example, processing circuitry 208 may be configured to detect ECAPs elicited from respective control stimulation pulses.

The pulse width of the control pulses may be shorter than the pulse width of the informed pulses to reduce or prevent a sensed electrical artifact from control pulses from obscuring the ECAP signals (put another way, the pulse width of the informed pulses may be longer than the pulse width of the control pulses). For example, the control pulses may be less than approximately 300 microseconds (μs). In one example, the control pulse may be a bi-phasic pulse having a positive phase of approximately 100 μs and a negative phase of approximately 100 μs separated by an interphase interval of approximately 30 μs. In this manner, stimulation electrodes at one end of a lead may deliver the control pulse and electrodes at the other end of the same lead may sense the ECAP signal without, or with minimal, interference from the control pulse itself. In general, the term "pulse width" herein refers to the collective duration of every phase, and interphase interval when appropriate, of a single pulse. A single pulse may include a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 μs, a negative phase lasting 100 μs, and an interphase interval lasting 30 μs defines a pulse width of 230 μs).

Processing circuitry 208 may be configured to compare one or more characteristics of ECAPs sensed by sensing circuitry 206 with target ECAP characteristics stored in memory 216 (e.g., patient ECAP characteristics 222). For example, processing circuitry 208 can determine the amplitude of each ECAP signal received at sensing circuitry 206, and processing circuitry 208 can determine the representative amplitude of at least one respective ECAP signal and compare the representative amplitude of a series of ECAP signals to a target ECAP characteristic value.

In other examples, processing circuitry 208 may use the representative amplitude of the at least one respective ECAP to change other parameters of stimulation pulses (e.g., informed pulses and/or control pulses) to be delivered, such as pulse width, pulse frequency, and pulse shape. All of these parameters may contribute to the intensity of the stimulation pulses, and changing one or more of these parameter values may effectively adjust the stimulation pulse intensity to compensate for the changed distance between the stimulation electrodes and the nerves indicated by the characteristic (e.g., a representative amplitude) of the ECAP signals.

In some examples, leads 230 may be linear 8-electrode leads (not pictured); sensing and stimulation delivery may each be performed using a different set of electrodes. In a linear 8-electrode lead, each electrode may be numbered consecutively from 0 through 7. For instance, a pulse may be generated using electrode 1 as a cathode and electrodes 0 and 2 as anodes (e.g., a guarded cathode), and a respective ECAP signal may be sensed using electrodes 6 and 7, which are located on the opposite end of the electrode array. This strategy may minimize the interference of the stimulation pulse with the sensing of the respective ECAP. Other electrode combinations may be implemented, and the electrode combinations may be changed using the patient programmer via telemetry circuitry 212. For example, stimulation electrodes and sensing electrodes may be positioned closer together. Shorter pulse widths for the nontherapeutic pulses may allow the sensing electrodes to be closer to the stimulation electrodes.

In one example, sensor 210 may detect a change in posture state, including activity or a change in posture of the patient. Processing circuitry 208 may receive an indication from sensor 210 that the activity level or posture of the patient is changed, and processing circuitry 208 can initiate or change the delivery of the plurality of pulses according to stimulation parameter settings 220. For example, processing circuitry 208 may increase the frequency of pulse delivery and respective ECAP sensing in response to receiving an indication that the patient activity has increased, which may indicate that the distance between electrodes and nerves will likely change. Alternatively, processing circuitry 208 may decrease the frequency of pulse delivery and respective ECAP sensing in response to receiving an indication that the patient activity has decreased. In some examples, one or more therapy parameters (e.g., frequency, amplitude, slew rate, pulse width, or the like) may be adjusted (e.g., increased or decreased) in response to receiving an indication that the patient posture state has changed. Processing circuitry 208 can update patient posture state data 218 and growth curve data 224 according to the signal received from sensor 210.

Figure 3:
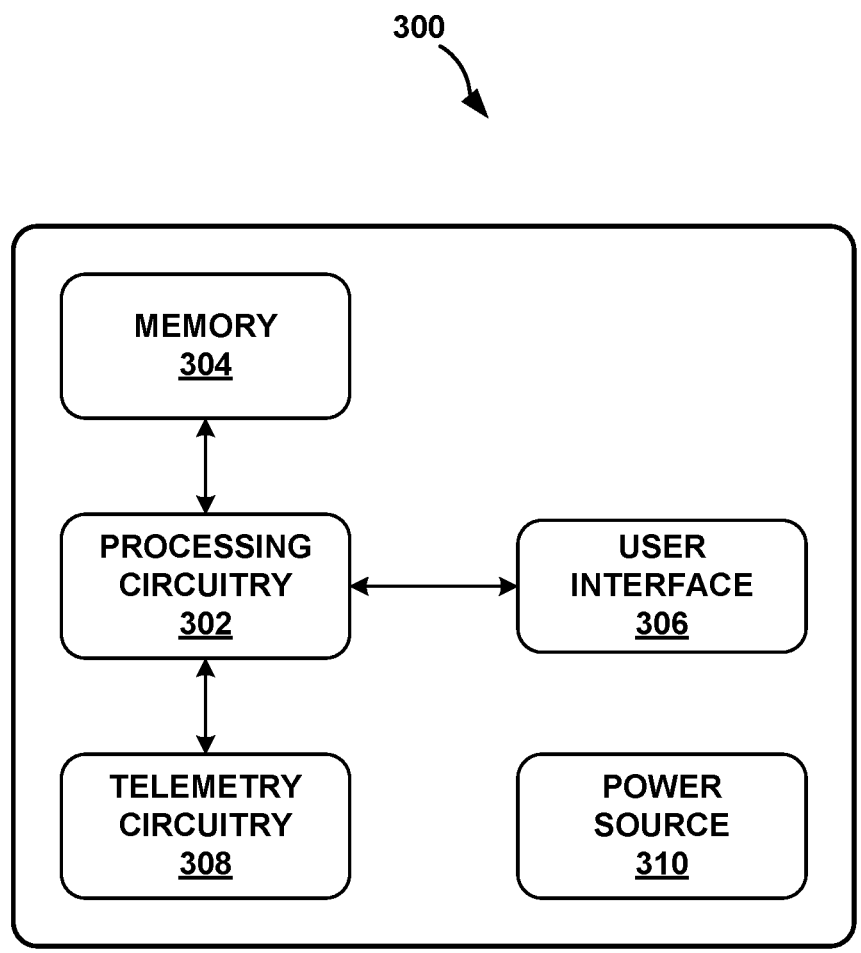
FIG. 3 is a block diagram of the example external programmer of FIG. 1.

FIG. 3 is a block diagram of the example external programmer 300. External programmer 300 may be an example of external programmer 104 of FIG. 1. Although programmer 300 may generally be described as a hand-held device, external programmer 300 may be a larger portable device or a more stationary device. In addition, in some examples, external programmer 300 may be included as part of an external charging device or include the functionality of an external charging device. As illustrated in FIG. 3, external programmer 300 may include a processing circuitry 302, memory 304, user interface 306, telemetry circuitry 308, and power source 310. Storage device 304 may store instructions that, when executed by processing circuitry 302, cause processing circuitry 302 and external programmer 300 to provide the functionality ascribed to external programmer 300 throughout this disclosure. Each of these components, circuitry, or modules, may include electrical circuitry that can perform some, or all of the functionality described herein. For example, processing circuitry 302 may include processing circuitry to perform the processes discussed with respect to processing circuitry 302.

In general, programmer 300 comprises any suitable arrangement of hardware, alone or in combination with software and/or firmware, to perform the techniques attributed to programmer 300, and processing circuitry 302, user interface 306, and telemetry circuitry 308 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 304, such as RAM, ROM, PROM, EPROM, EEPROM, flash memory, a hard disk, a CD-ROM, comprising executable instructions for causing the one or more processors to perform the actions attributed to them. Moreover, although processing circuitry 302 and telemetry circuitry 308 are described as separate, in some examples, processing circuitry 302 and telemetry circuitry 308 are functionally integrated. In some examples, processing circuitry 302 and telemetry circuitry 308 correspond to individual hardware units, such as ASICs, DSPs, FPGAs, or other hardware units.

Memory 304 (e.g., a storage device) may store instructions that, when executed by processing circuitry 302, cause processing circuitry 302 and programmer 300 to provide the functionality ascribed to programmer 300 throughout this disclosure. For example, memory 304 may include instructions that cause processing circuitry 302 to obtain a stimulation parameter setting from memory, select a spatial electrode movement pattern, or receive a user input and send a corresponding command to programmer 300, or instructions for any other functionality. In addition, memory 304 may include a plurality of stimulation parameter settings, where each setting includes a parameter set that defines electrical stimulation. Memory 304 may also store data received from a medical device (e.g., IMD 110). For example, memory 304 may store ECAP related data recorded at a sensing circuitry of the medical device, and memory 304 may also store data from one or more sensors of the medical device.

User interface 306 may include a button or keypad, lights, a speaker for voice commands, a display, such as a liquid crystal (LCD), light-emitting diode (LED), or organic light-emitting diode (OLED). In some examples the display may be a touch screen. User interface 306 can display any information related to the delivery of electrical stimulation, identified patient behaviors, sensed patient parameter values, patient behavior criteria, or any other such information. External programmer 300 may receive user input (e.g., indication of when the patient changes posture states) via user interface 306. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. In other examples, user interface 306 may receive input from the patient and/or clinician regarding efficacy of the therapy, such as binary feedback, numerical ratings, textual input, etc. In some examples, processing circuitry 302 may interpret patient requests to change therapy as negative feedback regarding the current parameter values used to define therapy.

Telemetry circuitry 308 may support wireless communication between the medical device and programmer 300 under the control of processing circuitry 302. Telemetry circuitry 308 can communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 300 and IMD 110 include RF communication according to the 902.11 or Bluetooth specification sets or other standard or proprietary telemetry protocols. In this manner, other external devices may be capable of communicating with programmer 300 without needing to establish a secure wireless connection. As described herein, telemetry circuitry 308 can transmit a spatial electrode movement pattern or other stimulation parameter values to IMD 110 for delivery of electrical stimulation.

In some examples, selection of stimulation parameter settings (e.g., informed parameter values and/or control parameter values) may be transmitted to the medical device for delivery to the patient. In other examples, stimulation parameter settings may include medication, activities, or other instructions that the patient must perform themselves or a caregiver perform for patient 102. In some examples, external programmer 300 may provide visual, audible, and/or tactile notifications that indicate there are new instructions. External programmer 300 may require receiving user input acknowledging that the instructions have been completed in some examples.

According to the techniques of the disclosure, user interface 306 of external programmer 300 receives an indication from a clinician instructing a processor of the medical device to update one or more patient posture state settings, gain values, growth curve settings, or stimulation parameter settings. Updating the posture state settings, gain values, growth curve settings may cause the stimulation parameter settings to update as well, including changing one or more parameter values of the informed stimulation pulses delivered by the medical device according to the settings, such as pulse amplitude, pulse width, pulse frequency, electrode combination, and/or waveform shape. Gain values and/or growth curve settings may be based upon sensed ECAP signals, posture state data, and stimulation parameter data, in some examples. User interface 306 may also receive instructions from the clinician commanding any electrical stimulation.

Power source 310 can deliver operating power to various components of programmer 300. Power source 310 may be the same as or substantially similar to power source 214. Power source 310 may include a battery and a power generation circuit to produce the operating power. In some examples, the battery is rechargeable to allow extended operation. Recharging may be accomplished by electrically coupling power source 310 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
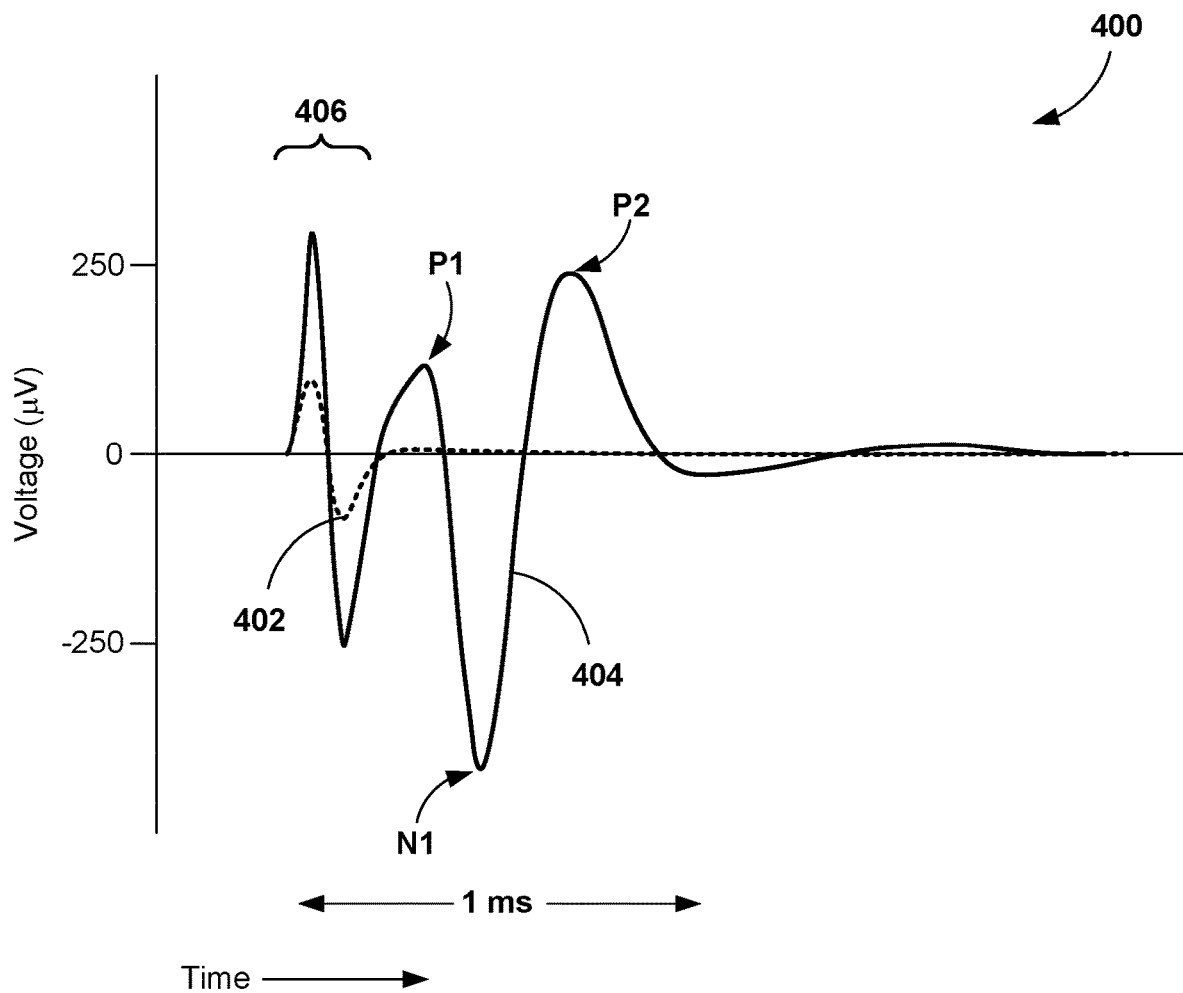
FIG. 4 is a graph of an example ECAP signal sensed from a stimulation pulse.

FIG. 4 is a graph 400 of an example ECAP signals sensed for respective stimulation pulses (e.g., a control pulse). As shown in FIG. 3, graph 400 shows example ECAP signal 402 (dotted line) and ECAP signal 404 (solid line). Each of ECAP signals 402 and 404 may be sensed from control pulses that were delivered from a guarded cathode and bi-phasic pulses including an interphase interval between each positive and negative phase of the pulse. The guarded cathode of the stimulation electrodes is located at the end of an 8-electrode lead while two sensing electrodes are provided at the other end of the 8-electrode lead. ECAP signal 402 illustrates the voltage amplitude sensed as a result from a sub-threshold stimulation pulse. Peaks 406 of ECAP signal 402 are detected and represent the artifact of the delivered pulse. However, no propagating signal is detected after the artifact in ECAP signal 404 because the pulse was sub-threshold.

In contrast to ECAP signal 402, ECAP signal 404 represents the voltage amplitude detected from a supra-threshold stimulation pulse. Peaks 406 of ECAP signal 404 are detected and represent the artifact of the delivered pulse. After peaks 406, ECAP signal 404 also includes peaks P1, N1, and P2, which are three peaks representative of propagating action potentials from an ECAP. The example duration of the artifact and peaks P1, N1, and P2 is approximately 1 millisecond (ms). When detecting the ECAP of ECAP signal 404, different characteristics may be identified. For example, the characteristic of the ECAP may be the amplitude between N1 and P2. This N1-P2 amplitude can be detected even if the artifact impinges on P1, a relatively large signal, and the N1-P2 amplitude may be minimally affected by electronic drift in the signal. In other examples, the characteristic of the ECAP used to control pulses may be an amplitude of P1, N1, or P2 with respect to neutral or zero voltage. In some examples, the characteristic of the ECAP used to control pulses may be a sum of two or more of peaks P1, N1, or P2. In other examples, the characteristic of ECAP signal 404 may be the area under one or more of peaks P1, N1, and/or P2. In other examples, the characteristic of the ECAP may be a ratio of one of peaks P1, N1, or P2 to another one of the peaks. In some examples, the characteristic of the ECAP may be a slope between two points in the ECAP signal, such as the slope between N1 and P2. In other examples, the characteristic of the ECAP may be the time between two points of the ECAP, such as the time between N1 and P2. The time between two points in the ECAP signal may be referred to as a latency of the ECAP and may indicate the types of fibers being captured by the pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal increases with increased amplitude of the pulse, as long as the pulse amplitude is greater than the threshold such that nerves depolarize and propagate the signal. The target ECAP characteristic (e.g., the target ECAP amplitude) may be determined from the ECAP signal detected from a pulse when pulses are determined to deliver effective therapy to the patient. The ECAP signal thus is representative of the distance between the stimulation electrodes and the nerves appropriate for the stimulation parameter values of the pulses delivered at that time. Therefore, IMD 110 may attempt to use detected changes to the measured ECAP characteristic value to change stimulation pulse parameter values and maintain the target ECAP characteristic value during stimulation pulse delivery (e.g., informed pulses and/or control pulses). Alternatively, IMD 110 may attempt to prevent undesirable stimulation intensity by decreasing stimulation pulse intensity in response to the ECAP characteristic value exceeding a threshold ECAP characteristic value.

Figure 5A:
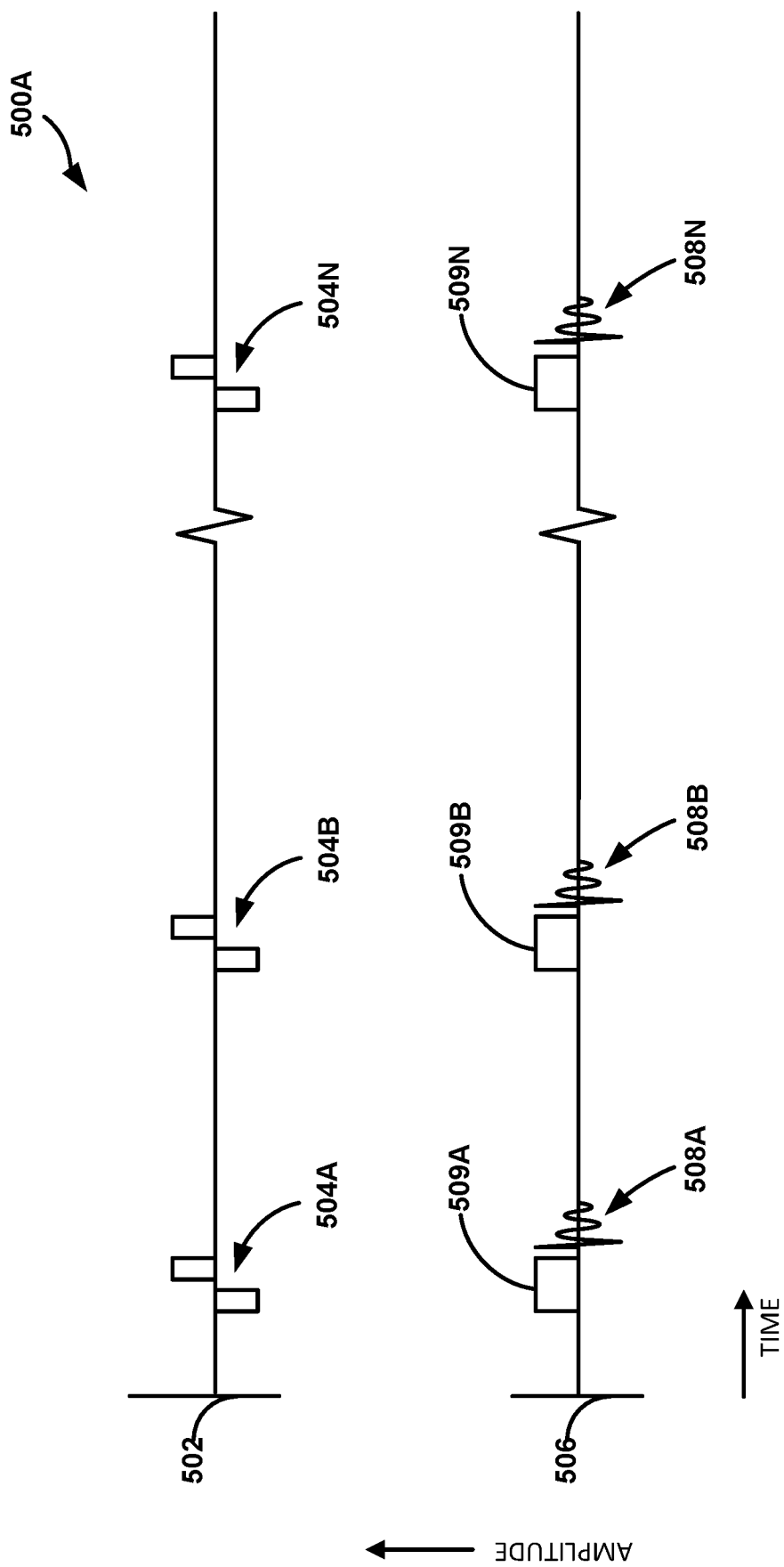
FIGS. 5A, 5B, 5C, and 5D are timing diagrams illustrating example electrical stimulation pulses and respective sensed ECAPs, in accordance with one or more techniques of this disclosure.

FIG. 5A is a timing diagram 500A illustrating one example of electrical stimulation pulses (e.g., control pulses) and respective sensed ECAPs, in accordance with one or more techniques of this disclosure. For convenience, FIG. 5A is described with reference to IMD 200 of FIG. 2. As illustrated, timing diagram 500A includes first channel 502, a plurality of control pulses 504A-504N (collectively "control pulses 504"), second channel 506, a plurality of respective ECAPs 508A-508N (collectively "ECAPs 508"), and a plurality of stimulation interference signals 509A-509N (collectively "stimulation interference signals 509"). In the example of FIG. 5A, control pulses 504 may or may not contribute to therapy for the patient. In any case, control pulses 504 may elicit respective ECAPs 508 for the purpose of determining relative neural recruitment due to the control pulses 504, which may be reflective as a growth curve specific to the posture state of the patient that was assumed with the ECAPs 508 were sensed.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Control pulses 504 may be electrical pulses delivered to the spinal cord of the patient by at least one of electrodes 232, 234, and control pulses 504 may be balanced biphasic square pulses with an interphase interval. In other words, each of control pulses 504 are shown with a negative phase and a positive phase separated by an interphase interval. For example, a control pulse 504 may have a negative voltage for the same amount of time and amplitude that it has a positive voltage. It is noted that the negative voltage phase may be before or after the positive voltage phase. Control pulses 504 may be delivered according to instructions stored in storage device 212 of IMD 200.

In some examples, each of control pulses 504 may be a part of a sweep of pulses configured to determine a relationship between the stimulation parameter values of the pulses and a characteristic value of the resulting respective ECAPs 508. For example, the relationship may be a growth curve of ECAP voltage amplitude versus pulse current amplitude. In this manner, each of control pulses 504 may differ from each other by a parameter value, such as an iteratively increasing current amplitude. Such sweeps may be performed for each posture state of a plurality of posture states in order to determine the growth curve, gain value, or some characteristic related to ECAPs for that posture state. In one example, control pulses 504 may have a pulse width of less than approximately 300 microseconds (e.g., the total time of the positive phase, the negative phase, and the interphase interval is less than 300 microseconds). In another example, control pulses 504 may have a pulse width of approximately 100 microseconds for each phase of the bi-phasic pulse. In some examples, the pulse width of control pulses 504 may be longer than 300 microseconds, as long as the pulse width does not interfere with the detection of the desired one or more features of the elicited ECAPs 508. As illustrated in FIG. 5A, control pulses 504 may be delivered via channel 502. Delivery of control pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to control pulses 504. ECAPs 508 are electrical signals which may propagate along a nerve away from the origination of control pulses 504. In one example, ECAPs 508 are sensed by different electrodes than the electrodes used to deliver control pulses 504. As illustrated in FIG. 5A, ECAPs 508 may be recorded on second channel 506. In some examples, ECAPs 508 may not be sensed after each control pulse 504.

Stimulation interference signals 509A, 509B, and 509N (e.g., the artifact of the control pulses) may be sensed by leads 230 and may be sensed during the same period of time as the delivery of control pulses 504. Since the interference signals may have a greater amplitude and intensity than ECAPs 508, any ECAPs arriving at IMD 200 during the occurrence of stimulation interference signals 509 may not be adequately sensed by sensing circuitry 206 of IMD 200. However, ECAPs 508 may be sufficiently sensed by sensing circuitry 206 because each ECAP 508, or at least a portion of ECAP 508 that includes one or more desired features of ECAP 508 that is used to detect the posture state and/or as feedback for control pulses 504, falls after the completion of each a control pulse 504. As illustrated in FIG. 5A, stimulation interference signals 509 and ECAPs 508 may be recorded on channel 506.

In some examples, IMD 200, for example, may deliver the entire group of control pulses 504 (e.g., a sweep) consecutively and without any other intervening pulses in order to detect ECAPs 508 from which respective characteristic values are determined. IMD 200 may then determine the relationship between the characteristic values from ECAPs 508 and the different parameter values of control pulses 504. In one example, the sweep of pulses 504 may be delivered by IMD 200 during a break in delivery of other types of control pulses.

Figure 5B:
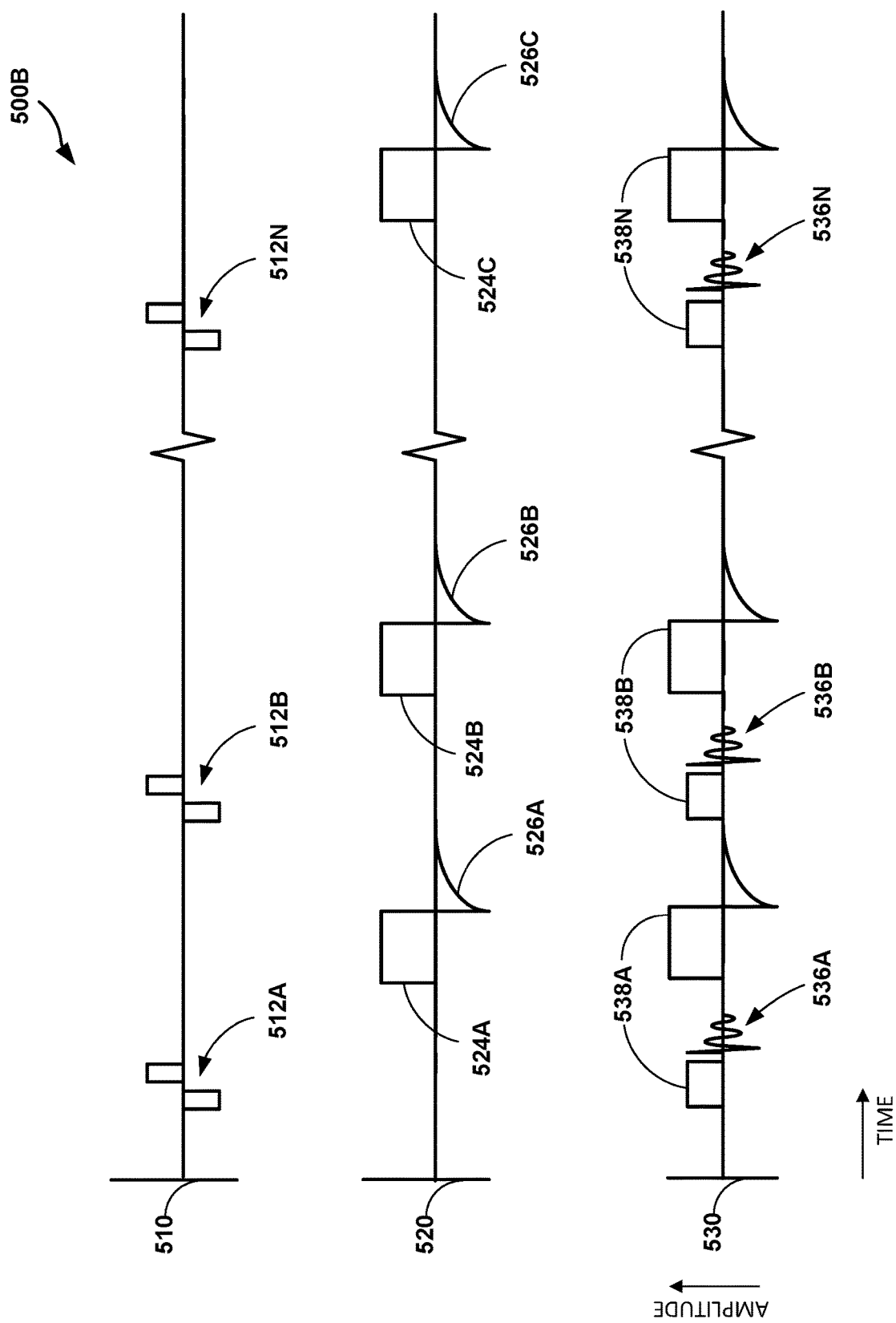

FIG. 5B is a timing diagram 500B illustrating another example of electrical stimulation pulses and respective sensed ECAPs, in accordance with one or more techniques of this disclosure. For convenience, FIG. 5B is described with reference to IMD 200 of FIG. 2. As illustrated, timing diagram 500B includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation interference signals 538A-538N (collectively "stimulation interference signals 538").

First channel 510 is a time/voltage (and/or current) graph indicating the voltage (or current) of at least one electrode of electrodes 232, 234. In one example, the stimulation electrodes of first channel 510 may be located on the opposite side of the lead as the sensing electrodes of third channel 530. Control pulses 512 may be electrical pulses delivered to the spinal cord of the patient by at least one of electrodes 232, 234, and control pulses 512 may be balanced biphasic square pulses with an interphase interval. In other words, each of control pulses 512 are shown with a negative phase and a positive phase separated by an interphase interval. For example, control pulse 512 may have a negative voltage for the same amount of time and amplitude that it has a positive voltage. It is noted that the negative voltage phase may be before or after the positive voltage phase. Control pulses 512 may be delivered according to control stimulation parameters stored in memory 216 of IMD 200, and the control stimulation parameters may be updated according to user input via an external programmer and/or may be updated according to a signal from sensor(s) 210. In one example, control pulses 512 may have a pulse width of less than approximately 300 microseconds (e.g., the total time of the positive phase, the negative phase, and the interphase interval is less than 300 microseconds). In another example, control pulses 512 may have a pulse width of approximately 100 microseconds for each phase of the bi-phasic pulse. As illustrated in FIG. 5B, control pulses 512 may be delivered via channel 510. Delivery of control pulses 512 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 520 is a time/voltage (and/or current) graph indicating the voltage (or current) of at least one electrode of electrodes 232, 234 for the informed pulses. In one example, the electrodes of second channel 520 may partially or fully share common electrodes with the electrodes of first channel 510 and third channel 530. Informed pulses 524 may also be delivered by the same leads 230 that are configured to deliver control pulses 512. Informed pulses 524 may be interleaved with control pulses 512, such that the two types of pulses are not delivered during overlapping periods of time. However, informed pulses 524 may or may not be delivered by exactly the same electrodes that deliver control pulses 512. Informed pulses 524 may be monophasic pulses with pulse widths of greater than approximately 300 microseconds and less than approximately 1000 microseconds. In fact, informed pulses 524 may be configured to have longer pulse widths than control pulses 512. As illustrated in FIG. 6B, informed pulses 524 may be delivered on channel 520.

Informed pulses 524 may be configured for passive recharge. For example, each informed pulse 524 may be followed by a passive recharge phase 526 to equalize charge on the stimulation electrodes. Unlike a pulse configured for active recharge, wherein remaining charge on the tissue following a stimulation pulse is instantly removed from the tissue by an opposite applied charge, passive recharge allows tissue to naturally discharge to some reference voltage (e.g., ground or a rail voltage) following the termination of informed pulse 524. In some examples, the electrodes of the medical device may be grounded at the medical device body. In this case, following the termination of informed pulse 524, the charge on the tissue surrounding the electrodes may dissipate to the medical device, creating a rapid decay of the remaining charge at the tissue following the termination of the pulse. This rapid decay is illustrated in passive recharge phases 526. Passive recharge phase 526 may have a duration in addition to the pulse width of the preceding informed pulse 524. In other examples (not pictured in FIG. 5B), informed pulses 524 may be bi-phasic pulses having a positive and negative phase (and, in some examples, an interphase interval between each phase) which may be referred to as pulses including active recharge. Informed pulse 524 that is a bi-phasic pulse may or may not have a following passive recharge phase.

Third channel 530 is a time/voltage (and/or current) graph indicating the voltage (or current) of at least one electrode of electrodes 232, 234. In one example, the electrodes of third channel 530 may be located on the opposite side of the lead as the electrodes of first channel 510. ECAPs 536 may be sensed at electrodes 232, 234 from the spinal cord of the patient in response to control pulses 512. ECAPs 536 are electrical signals which may propagate along a nerve away from the origination of control pulses 512. In one example, ECAPs 536 are sensed by different electrodes than the electrodes used to deliver control pulses 512. As illustrated in FIG. 5B, ECAPs 536 may be recorded on third channel 530.

Stimulation interference signals 538A, 538B, and 538N (e.g., the artifact of the stimulation pulses) may be sensed by leads 230 and may be sensed during the same period of time as the delivery of control pulses 512 and informed pulses 524. Since the interference signals may have a greater amplitude and intensity than ECAPs 536, any ECAPs arriving at IMD 200 during the occurrence of stimulation interference signals 538 may not be adequately sensed by sensing circuitry 206 of IMD 200. However, ECAPs 536 may be sufficiently sensed by sensing circuitry 206 because each ECAP 536 falls after the completion of each control pulse 512 and before the delivery of the next informed pulse 524. As illustrated in FIG. 5B, stimulation interference signals 538 and ECAPs 536 may be recorded on channel 530.

Two or more control pulses 512 may be delivered during each time event (e.g., window) of a plurality of time events, and each time event represents a time between two consecutive informed pulses 524. For example, during each time event, a first control pulse may be directly followed by a first respective ECAP, and subsequent to the completion of the first respective ECAP, a second control pulse may be directly followed by a second respective ECAP. Informed pulses may commence following the second respective ECAP.

Consecutive informed pulses 524 may be delivered without intervening control pulse 512. For example, control pulses 512 may not be delivered during each time event (or window) of the plurality of time events, wherein each time event represents a time between two consecutive informed pulses 524. In any case, informed pulses 524 can be delivered according to a predetermined frequency, and control pulses 512 may be delivered at any time between the informed pulses.

Figure 5C:
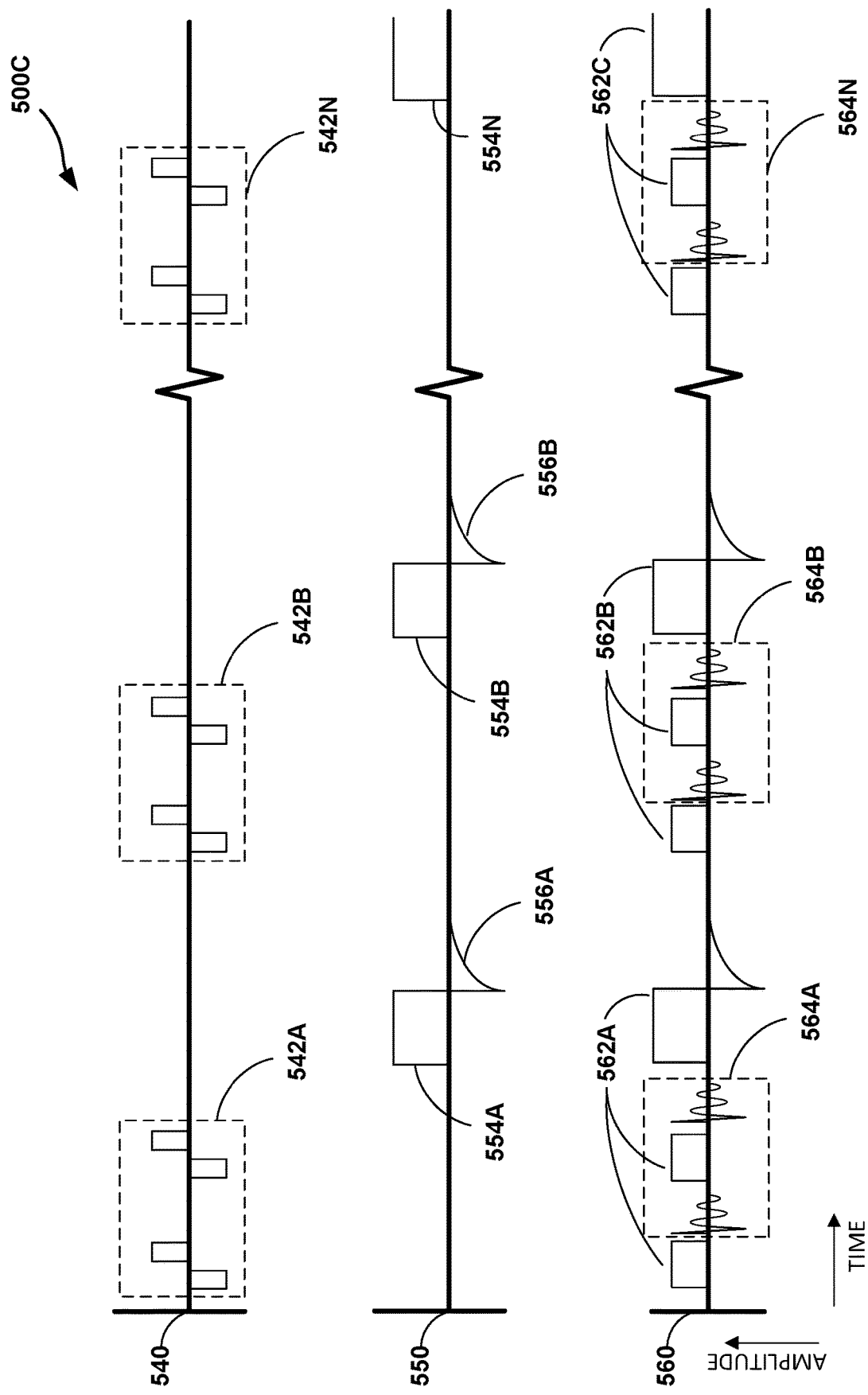

FIG. 5C is a timing diagram 500C illustrating another example of electrical stimulation pulses and respective ECAPs according to the techniques of the disclosure. For convenience, FIG. 5C is described with reference to IMD 200 of FIG. 2A. As illustrated, timing diagram 500C includes first channel 540, a plurality of control pulses 542A-542N (collectively "control pulses 542"), second channel 550, a plurality of informed pulses 554A-554N (collectively "informed pulses 554") including passive recharge phases 556A-556N (collectively "passive recharge phases 556"), third channel 560, a plurality of respective ECAPs 564A-564N (collectively "ECAPs 564"), and a plurality of stimulation interference signals 562A-562N (collectively "stimulation interference signals 562"). FIG. 5C may be substantially similar to FIG. 5B, except for the differences detailed below.

Two or more (e.g. two) control pulses 542 may be delivered during each time event (e.g., window) of a plurality of time events, and each time event represents a time between two consecutive informed pulses 554. For example, during each time event, a first control pulse of control pulses 542A may be directly followed by a first respective ECAP of ECAPs 564A, and subsequent to the completion of the first respective ECAP, a second control pulse of control pulses 542A may be directly followed by a second respective ECAP of ECAPs 564A. Informed pulses 554 may commence following the second respective ECAP. In other examples not illustrated here, three or more control pulses 542 may be delivered, and respective ECAP signals sensed, during each time event of the plurality of time events.

Figure 5D:
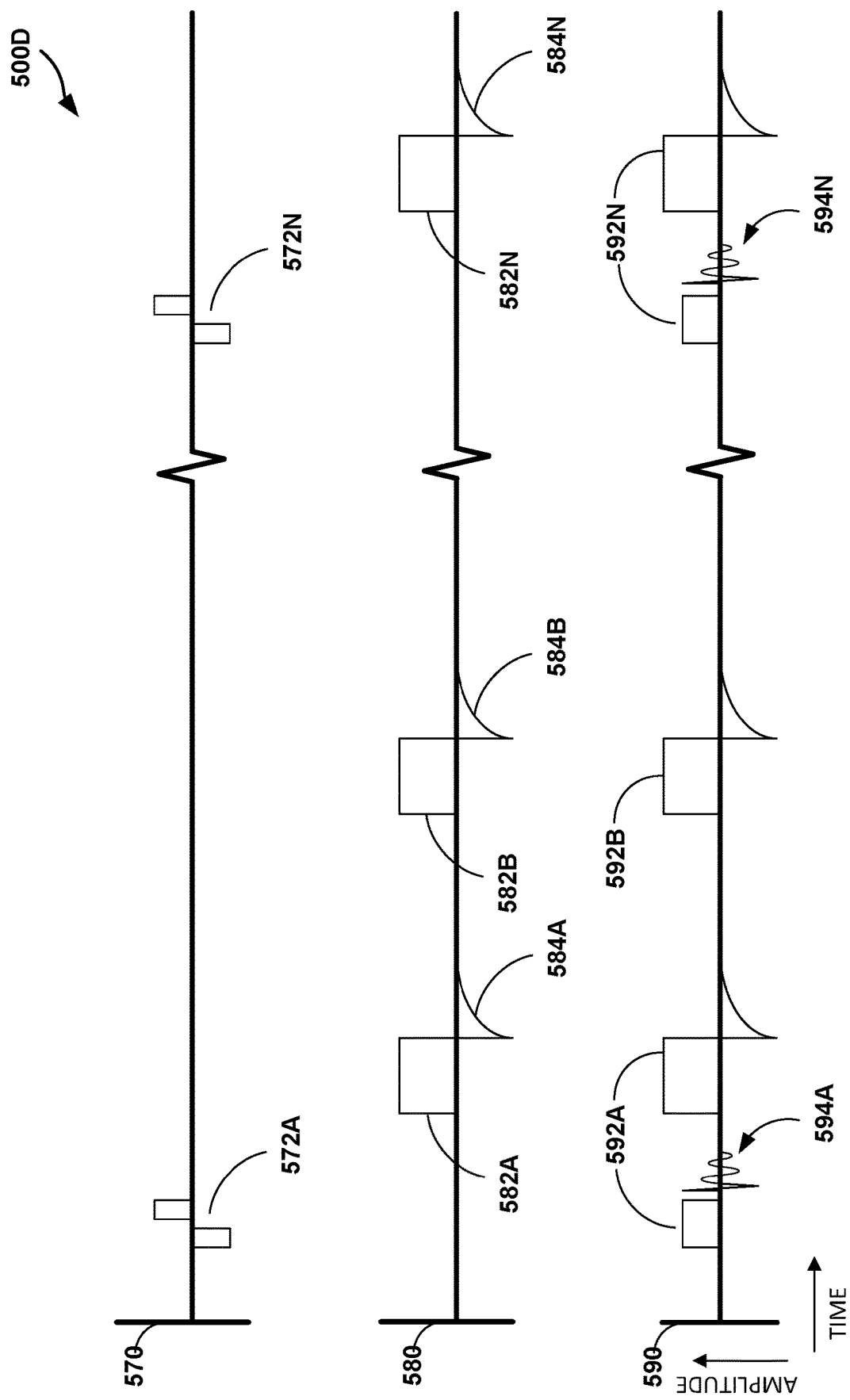
Figure 6:
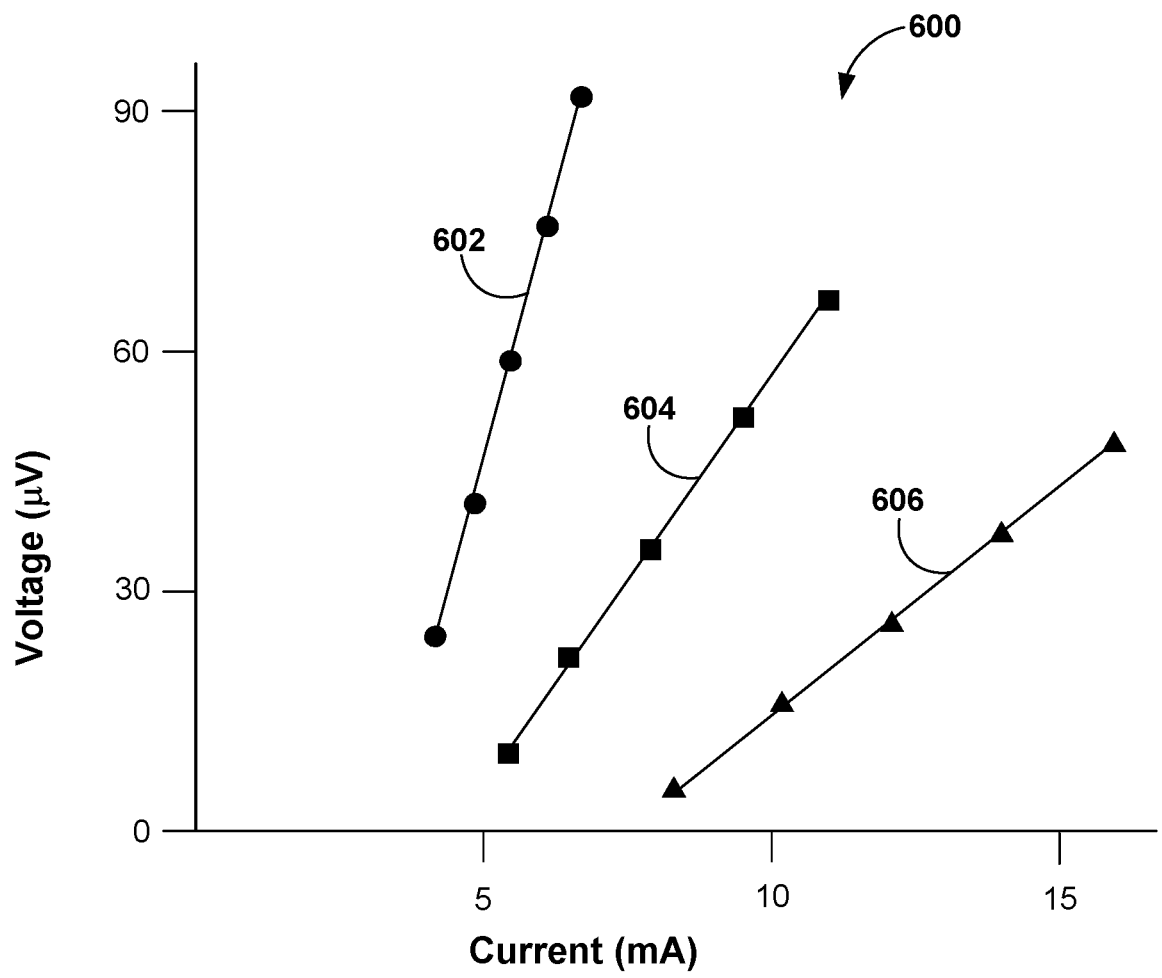
FIG. 6 is a graph of example growth curves derived from sensed ECAPs during respective posture states.

FIG. 5D is a timing diagram 500D illustrating another example of electrical stimulation pulses and respective ECAPs according to the techniques of the disclosure. For convenience, FIG. 5D is described with reference to IMD 200 of FIG. 2A. As illustrated, timing diagram 500D includes first channel 570, a plurality of control pulses 572A-572N (collectively "control pulses 572"), second channel 580, a plurality of informed pulses 582A-582N (collectively "informed pulses 582") including passive recharge phases 584A-584N (collectively "passive recharge phases 584"), third channel 590, a plurality of respective ECAPs 594A-594N (collectively "ECAPs 594"), and a plurality of stimulation interference signals 592A-592N (collectively "stimulation interference signals 592"). FIG. 6 may be substantially similar to FIGS. 5B and 5C, except for the differences detailed below.

In previous examples illustrated in FIG. 5B and FIG. 5C, at least one control pulse was delivered and interleaved between each pair of consecutive informed pulses. However, in some examples, control pulses 572 are not delivered during each time event (or window) of the plurality of time events, wherein each time event represents a time between two consecutive informed pulses 582. As illustrated in the example of FIG. 5D, a control pulse 572 is not delivered following informed pulse 582A and preceding informed pulse 582B. In other words, consecutive informed pulses 582A and 582B may be delivered without an intervening control pulse. In any case, informed pulses are delivered according to a predetermined frequency, and control pulses may be delivered at any time between the informed pulses.

In some examples, the parameter values of both informed pulse 582A and informed pulse 582B may be the same because they are defined by the same stimulation program. In other examples, informed pulse 582A and informed pulse 582B may have at least one stimulation parameter that differs in value, such as a different amplitude, pulse width, pulse frequency, or electrode combination. In this manner, informed pulse 582A may be a part of a first stimulation program while informed pulse 582B may be part of a second stimulation program that is different than the first stimulation program. Processing circuitry 214 may thus delivery informed pulses from two or more different stimulation programs, where processing circuitry 214 uses the detected ECAP signal from the same control pulse (e.g., control pulse 572A) to "inform" or otherwise adjust one or more parameter values of the informed pulses in multiple stimulation programs (e.g., both of informed pulses 582A and 582B). This concept of multiple stimulation programs may be applied to any informed pulses described herein.

Control pulses 572 may be administered according to control stimulation parameters stored in memory 216. Processing circuitry 214 may be configured to update the control pulse delivery instructions according to user input via telemetry circuitry 213, and also by a signal from sensor 216. For example, a clinician may operate a patient programmer and send a signal to telemetry circuitry 213 including instructions for updating the control pulse parameters. The clinician may set control stimulation to any of the examples illustrated in FIGS. 5A-5D, and the clinician also may customize control stimulation to a configuration not illustrated in FIGS. 5A-5D. The clinician may elect to cease control stimulation or commence control stimulation at any time. In some examples, a detection that the patient's posture or activity level has changed will initiate control stimulation.

FIG. 6 is a graph 600 of example growth curves 602, 604, and 606 of sensed ECAPs from respective stimulation pulse amplitudes. Graph 600 illustrates example ECAPs shown as dots (growth curve 602), squares (growth curve 604), and triangles (growth curve 606) for respective different current amplitudes of stimulation pulses. ECAPs will sometimes not be generated until the control stimulation pulse amplitude reaches a threshold, approximately at 4.5 mA current in the example of FIG. 6. Then, as the current amplitude is increased, the ECAP amplitude also increases approximately linearly. This linear relationship is shown by growth curves 602, 604, 606. Besides growth curves varying based on the posture state of the patient, the slope may vary for each patient based on the type of electrodes implanted, where the electrodes are implanted, the sensitivity of the patient's neurons to stimulation, neurological dysfunction, or other factors.

While a patient is in a given posture state, sensed ECAPs may be detected for control stimulation pulses with different current amplitudes. For example, each growth curve 602, 604, and 606 may be for a single posture state, e.g., supine, prone, sitting, standing, or lying on the right side or left side. If a patient changes posture states, the growth curve can also change. When a patient changes posture states, e.g., supine to standing and standing to running, the corresponding growth curve can change as well. For example, growth curve 602 may be associated with a supine posture state, growth curve 604 may be associated with a sitting posture state, and growth curve 606 may be associated with a prone posture state. In some examples, a patient may change posture states, but the same growth curve, or gain value, may apply to the different posture state.

The slope of the growth curves 602, 604, and 606 that linearly increase may indicate the relationship between sensed ECAP amplitudes and control pulse amplitudes. In some examples, the gain value used to increase or decrease control stimulation parameter values and/or informed stimulation pulse values may be inversely proportional to the slope of the growth curve of values of the characteristic of ECAP signals (e.g., an amplitude such as the N1-P2 amplitude or the amplitude of any peak of the ECAP signal) elicited from respective control stimulation pulses delivered to the patient and at least partially defined by different values of a control stimulation parameter (e.g., current amplitude, voltage amplitude, or pulse width). For example, the gain value for a patient may be used to dynamically adjust pulse amplitude based on the sensed ECAP amplitudes. In some examples, the gain may be approximated for a patient based on historical data for similar patients. In other examples, the system may generate a custom growth curve and gain specific to the patient before starting therapy with the system.

Figure 7:
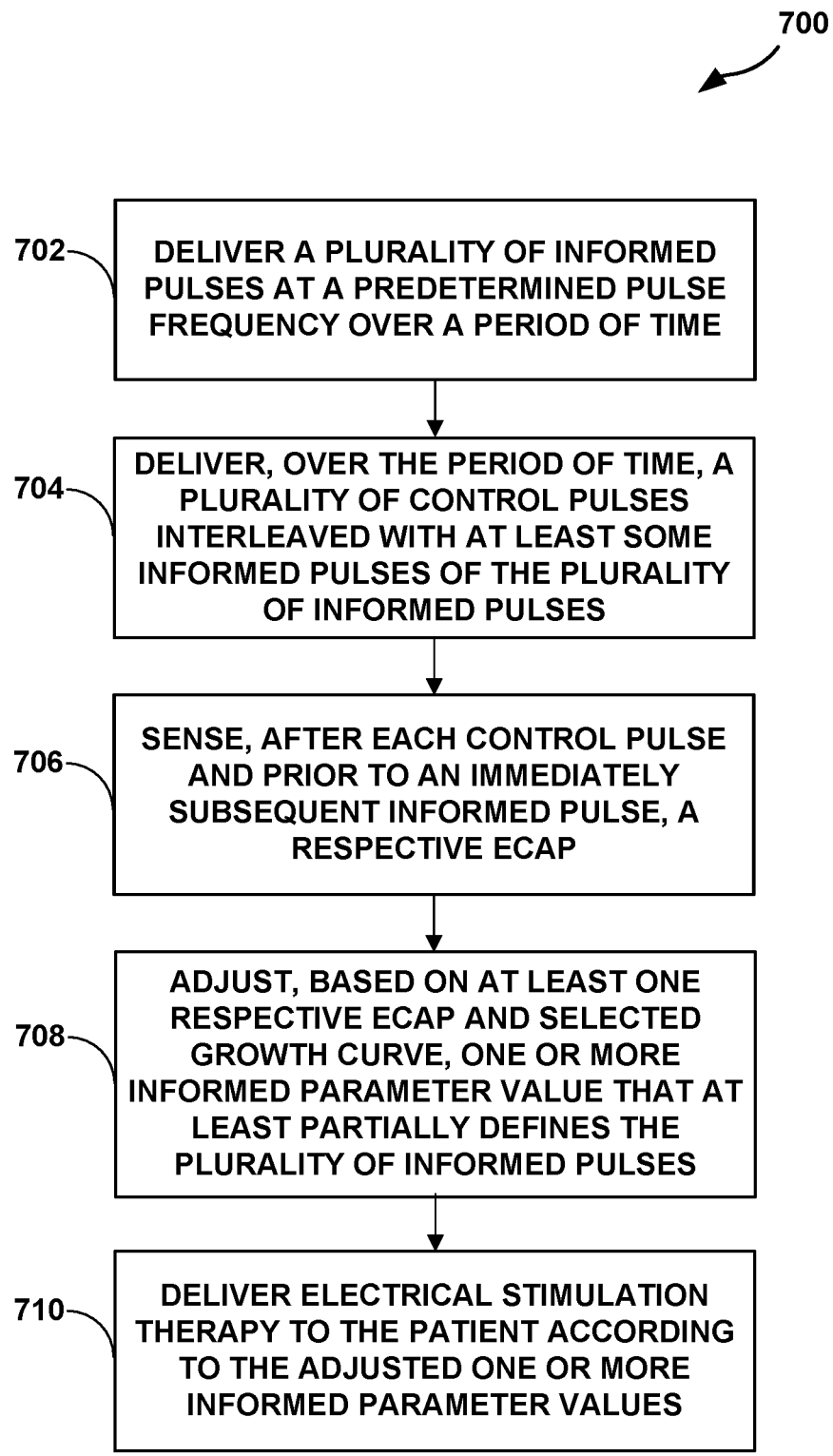
FIG. 7 is a flowchart illustrating an example operation for delivering control stimulation pulses and informed stimulation pulses, in accordance with one or more techniques of this disclosure.

FIG. 7 is a flowchart illustrating an example operation 700 for informed delivery according to the techniques of this disclosure. For convenience, FIG. 7 is described with respect to processing circuitry 208 of IMD 200 of FIG. 2. However, the techniques of FIG. 7 may be performed by different components of IMD 200 or by additional or alternative medical devices in some examples.

In the example of FIG. 7, IMD 200 delivers electrical stimulation therapy to patient 102, the electrical stimulation therapy comprising a plurality of informed pulses at a predetermined pulse frequency over a period of time (702). Furthermore, IMD 200 delivers, over the period of time, a plurality of control pulses interleaved with at least some informed pulses of the plurality of informed pulses (704). For example, one or more control pulses may be delivered between consecutive informed pulses. As another example, one or more informed pulses may be delivered between consecutive control pulses. IMD 200 may sense, after each control pulse and prior to an immediately subsequent informed pulse of the plurality of informed pulses, a respective ECAP (706). Subsequent to the sensing, IMD 200 may adjust, based on at least one respective ECAP and a selected growth curve, one or more informed parameter values that at least partially define the plurality of informed pulses of the electrical stimulation therapy (708). IMD 200 may also determine the current posture state of the patient and select the growth curve associated with the determined posture state. IMD 200 may compare a value of a characteristic of the sensed ECAP to a target ECAP characteristic value and adjust the informed pulses and, in some examples, the control pulses to maintain the target ECAP characteristic value. As discussed herein, IMD 200 may update the growth curve, continuously or non-continuously, to adjust for different posture states of patient 102. IMD 200 then delivers, via electrodes 108, the electrical stimulation therapy to spinal cord 106 of patient 102 according to the adjusted one or more informed parameter values (710).

Figure 8:
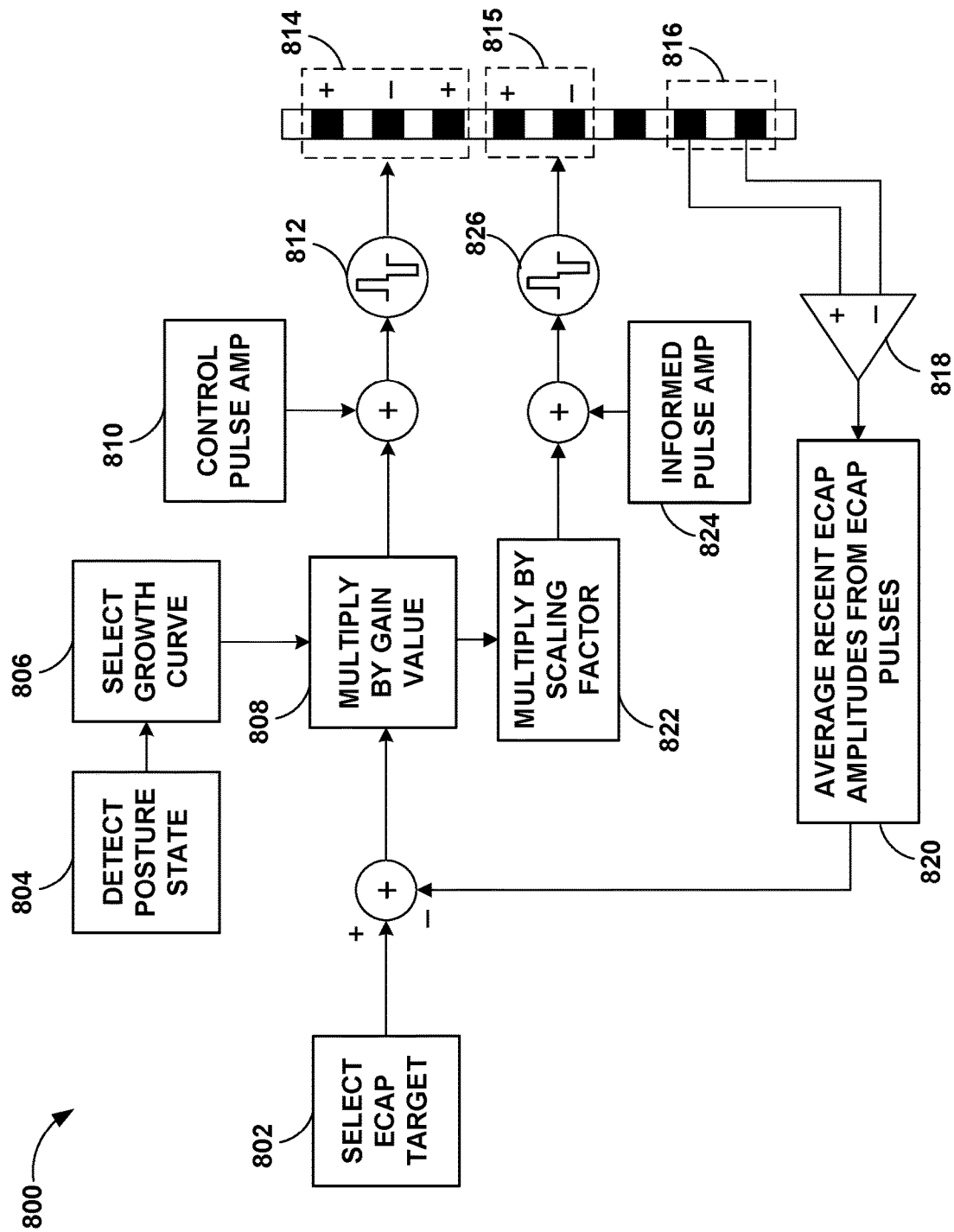
FIG. 8 is a diagram illustrating an example technique for adjusting electrical stimulation therapy.

FIG. 8 is a diagram illustrating an example technique 800 for adjusting stimulation therapy. As shown in the example of FIG. 8, the system, such as IMD 200 or any other device or system described herein, may dynamically adjust pulse amplitude (or other parameter) based on the gain value representing the patient sensitivity to stimulation. Processing circuitry 208 of IMD 200 may control stimulation generator 204 to deliver a stimulation pulses, such as informed pulses and control pulses, to a patient. Processing circuitry 208 may then control sensing circuitry 206 to sense an ECAP signal elicited by the control pulse and then identify a characteristic of the ECAP signal (e.g., an amplitude of the ECAP signal). Processing circuitry 208 may then determine, based on the characteristic of the ECAP signal and a gain value associated with a growth curve, a parameter value (e.g., an amplitude, pulse width value, pulse frequency value, and/or slew rate value) that at least partially defines stimulation pulses, such as control pulses and informed pulses. Processing circuitry 208 may then control stimulation generator 204 to deliver the informed pulses and control pulses according to the determined stimulation parameters.

As shown in FIG. 8, control pulse 812 is delivered to the patient via electrode combination 814, shown as a guarded cathode of three electrodes. The resulting ECAP is sensed by the two electrodes at the opposing end of the lead of electrode combination 816 fed to a differential amplifier 818. For each sensed ECAP, processing circuitry 208 may measure an amplitude of a portion of the ECAP signal, such as the N1-P2 voltage amplitude from the portion of the ECAP signal. Processing circuitry 208 may average the recently measured ECAP amplitudes, such as averaging the most recent, and consecutive, 2, 3, 4, 5, 6, or more ECAP amplitudes. In some examples, the average may be a mean or median value. In some examples, one or more ECAP amplitudes may be ignored from the calculations if the amplitude value is determined to be an error. The measured amplitude (or average measured amplitude) is then subtracted from the selected target ECAP amplitude 802 to generate a differential amplitude. The selected target ECAP amplitude 802 may be determined from an ECAP sensed when the physician or patient initially discovers effective therapy from the informed pulses and/or control pulses. This target ECAP amplitude 802 may essentially represent a reference distance between the stimulation electrodes and the target neurons (e.g., the spinal cord for the case of SCS).

The differential amplitude is then multiplied by the gain value for the patient to generate a differential value 808. Processing circuitry 208 may detecting patient posture state 804 at varying intervals including, e.g., periodic time intervals, at certain steps of the technique 800, in response to a trigger event, or continuously. For example, processing circuitry 208 may be continuously detecting posture state 804 of the patient in order to select a growth curve 806 that is associated with the detected posture state. Once the growth curve is selected 806, a gain value can be determined to generate the differential value 808. In other examples, processing circuitry 208 may select the gain value directly from the detected posture state instead of first selecting the associated growth curve. Processing circuitry 208 may add the differential value to the ECAP pulse amplitude to generate the new, or adjusted, control pulse amplitude 810 that at least partially defines the next pulse 812.

The following formulas may represent the function used to calculate the pulse amplitude of the next pulse 812. Equation 1 below represents an equation for calculating the new current amplitude using a linear function, wherein $A_C$ is the current pulse amplitude, D is the differential amplitude by subtracting the measured amplitude from the target ECAP amplitude, G is a real number for the gain value, and $A_N$ is the new pulse amplitude:

$$A_N = A_C + (D \times G) \quad (1)$$

In this manner, the gain value G may not change for a given input. Alternatively, processing circuitry 208 may calculate the gain value G such that the gain value varies according to one or more inputs or factors, such as posture state. In this manner, for a given input or set of inputs, processing circuitry 208 may change the gain value G. Equation 2 below represents an example linear function for calculating the gain value, wherein M is a multiplier, D is the differential amplitude by subtracting the measured amplitude from the target ECAP amplitude, and G is the gain value:

$$G = M \times D \quad (2)$$

Processing circuitry 208 may use the gain value G calculated in Equation 2 in Equation 1. This would result in Equation 1 being a non-linear function for determining the new current amplitude. According to Equation 2 above, the gain value G may be greater for larger differences between the measured amplitude and the target ECAP amplitude. Thus, gain value G will cause non-linear changes to the current amplitude. In this manner, the rate of change in the current amplitude will be higher for larger differences between the measured amplitude and the target ECAP amplitude and lower for smaller differences between the measured amplitude and the target ECAP amplitude. In other examples, a non-linear function may be used to calculate the gain value G.

To adjust the informed pulse amplitude, the differential value 808 is multiplied by a scaling factor 822 to generate the informed differential value. For example, the scaling factor may be the ratio of the previously delivered informed pulse amplitude to the previously delivered control pulse amplitude. The informed differential value is then added to the previously delivered informed pulse amplitude 824 to generate the new, or adjusted, informed pulse amplitude that at least partially defines the next informed pulse 826. The next informed pulse 826 is then delivered, interleaved with control pulse 812, to the patient via electrode combination 815. In some examples, at least two control pulses may be delivered, and at least two respective ECAP signals sensed, between consecutive informed pulses. This increased frequency of nontherapeutic pulses may allow the system to quickly adjust informed pulse amplitudes for any changes in the distance between electrodes and neurons. Although electrode combination 815 is different than electrode combinations 814 and 816, electrode combination 815 can be any set of electrodes on the lead as desired for therapy because the informed pulse is delivered in a non-overlapping fashion with control pulses and sensed ECAP signals.

The pulse width of the informed pulse may be greater than approximately 300 µs and less than approximately 1000 µs. In other examples, the pulse width of the informed pulse may be less than approximately 300 µs or greater than 1000 µs. The stimulation pulse may be a monophasic pulse followed a passive recharge phase. However, in other examples, the pulse may be a bi-phasic pulse that includes a positive phase and a negative phase. In some examples, a pulse may be less than 300 µs, but the following passive recharge phase or even an active recharge phase (of a bi-phasic pulse) may still obscure the detectable ECAP signal from that pulse.

In some examples, depending upon, at least in part, pulse width of the control pulse, IMD 200 may not sufficiently detect an ECAP signal because the stimulation pulse is also detected as an artifact that obscures the ECAP signal. If ECAPs are not adequately recorded, then ECAPs arriving at IMD 200 cannot be used to determine the efficacy of stimulation parameter settings, and electrical stimulation signals cannot be altered according to responsive ECAPs. In some examples, pulse widths of the control pulses may be less than approximately 300 µs, which may increase the number of ECAP signals detected. Similarly, high pulse frequencies may interfere with IMD 110 sufficiently detecting ECAP signals. For example, at pulse frequency values (e.g., greater than 1 kHz) that cause IMD 110 to deliver another control pulse before an ECAP from the previous pulse can be detected, IMD 110 may not be capable to detecting the ECAP.

Figure 9:
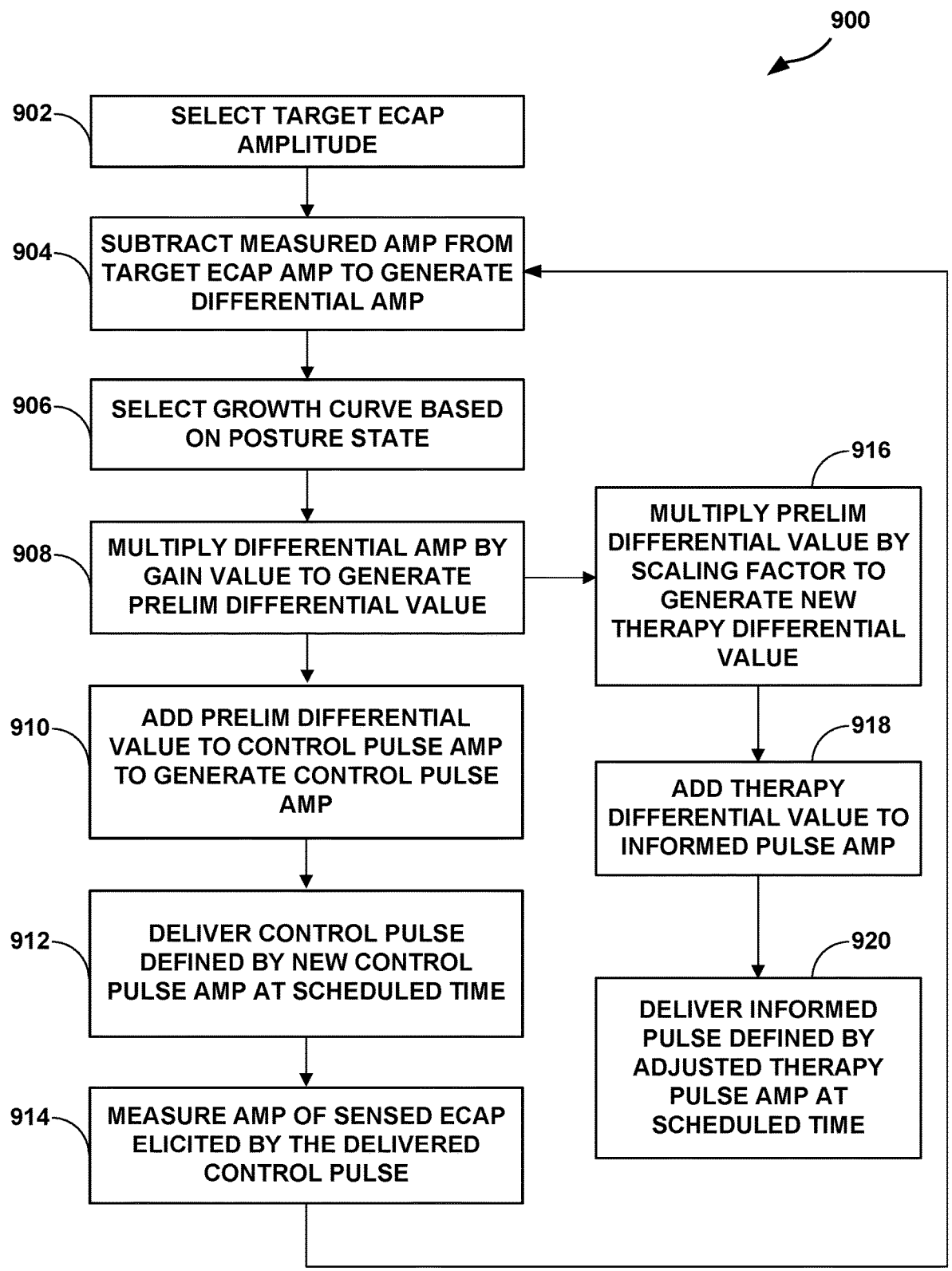
FIG. 9 is a flowchart illustrating an example operation for controlling stimulation therapy as described in FIG. 8.

FIG. 9 is a flowchart illustrating an example operation 900 for adjusting stimulation parameters, such as informed parameters and control parameters. IMD 200 and processing circuitry 208 will be described in the example of FIG. 9, but other IMDs such as IMD 110 or other devices or systems may perform, or partially perform, operation 900. Operation 900 may be similar to the diagram and discussion related to FIG. 8.

In the example of FIG. 9, processing circuitry 208 determines the target ECAP amplitude (902). The target ECAP amplitude may be determined based on sample stimulation initially delivered to the patient. The target ECAP amplitude may be the N1-P2 amplitude of the ECAP signal, but other measures of amplitude, such as amplitude of one or more different peaks in the ECAP signal may be used instead. Alternatively, the target ECAP amplitude may instead be a different characteristic of the ECAP signal such as the area under one or more peaks of the ECAP signal. In some examples, processing circuitry 208 is configured to automatically change the target ECAP amplitude over a period of time according to a predetermined function (e.g., a sinusoid function) in order to change the volume of neuron activation and, in some examples, the perceived sensation of the informed pulses.

Processing circuitry 208 receives a measured amplitude from the previously sensed ECAP signal. In order to use the ECAP signal as feedback to control the informed pulses of electrical stimulation therapy for the patient, processing circuitry 208 subtracts the measured amplitude from the target ECAP amplitude to generate a differential amplitude (904). In some examples, or as additional measured amplitudes are available from the process, processing circuitry 208 may average a certain number of recent measured amplitudes (e.g., two or more) to create a rolling average of measured ECAP amplitudes and subtract the average measured amplitudes from the target ECAP amplitude to smooth out variations between ECAP signals. The differential amplitude is thus a representation of how far of a distance the electrodes have moved relative to the neurons and can be used to adjust the amplitudes of the informed pulses and the control pulses to maintain consistent volume of neural activation of the neurons that provide relief to the patient.

Processing circuitry 208 can select a growth curve based on a posture state of the patient (906). Detecting patient posture state may be conducted at varying intervals including, e.g., periodic time intervals, at certain predetermined steps of method 800, or continuously. For example, processing circuitry 208 may continuously detect the posture state of the patient in order to select a growth curve for the currently occupied posture state of the patient. The patient posture state data can be stored in memory 216 continuously or non-continuously, including at set time intervals. Once the growth curve is selected, processing circuitry 208 can use the relationship between sensed and target parameter values to select new parameter values. In some examples, the processing circuitry 208 may determine the gain value from the growth curve. In other examples, processing circuitry 208 may select the gain value as directly associated with the identified posture state without first identifying a growth curve.

Processing circuitry 208 then multiplies the differential amplitude from block 904 by a gain value for the posture state of the patient to generate a preliminary differential value (908). The gain value may represent the slope of the growth curve for the patient. Processing circuitry 208 then uses the preliminary differential value to adjust the amplitudes of both subsequent informed pulses and control pulses (e.g., ECAP test pulses). Processing circuitry 208 adds the preliminary differential value to the control pulse amplitude to generate a new control pulse amplitude (910). Processing circuitry 208 then controls stimulation generation circuitry 208 to deliver a subsequent control pulse defined by the new control pulse amplitude at a scheduled time, such as according to the frequency of the control pulses or according to the next available window between informed pulses (912). Processing circuitry 208 also controls sensing circuitry 206 to measure the amplitude of the sensed ECAP elicited by the recently delivered control pulse (914) to use again as feedback in block 904.

In addition to adjusting the amplitude of the control pulses, processing circuitry 208 uses the preliminary amplitude to adjust the informed pulse amplitude. Processing circuitry 208 multiplies the differential value by a scaling factor to generate a new informed differential value (916). The scaling factor may be determined as the ratio between the amplitude of the most recently delivered informed pulse and the amplitude of the most recently delivered control pulse that elicited the ECAP signal used to generate the measured amplitude used in block 904. The scaling factor may scale up, or scale down, the differential amplitude for the informed pulses because the differential amplitude was generated based on amplitudes of control pulses. Processing circuitry 208 then adds the therapy differential value to the most recent informed pulse amplitude to generate a new informed pulse amplitude (918). Processing circuitry 208 then controls stimulation generator 204 to deliver the next informed pulse with the newly adjusted informed pulse amplitude at the scheduled time according to the predetermined pulse frequency of the informed pulses (920).

Although operation 900 is described for adjusting the amplitude of informed pulses and control pulses, a similar operation may be used to adjust other stimulation parameters in other examples. For example, parameters that contribute to the intensity of the informed pulses and control pulses may affect the volume of neural activation, such parameters as pulse width, pulse frequency, or even pulse shape (e.g., the amount of charge per pulse). Therefore, processing circuitry 208 can adjust a different parameter instead of, or in addition to, amplitude using the sensed ECAP signal elicited from the control pulses. For example, processing circuitry 208 may increase the pulse width of the informed pulses and control pulses in response to detecting a decreased ECAP amplitude. In addition, processing circuitry 208 can adjust parameters based on a change of patient posture state as well as a different growth curve being selected.

Figure 10:
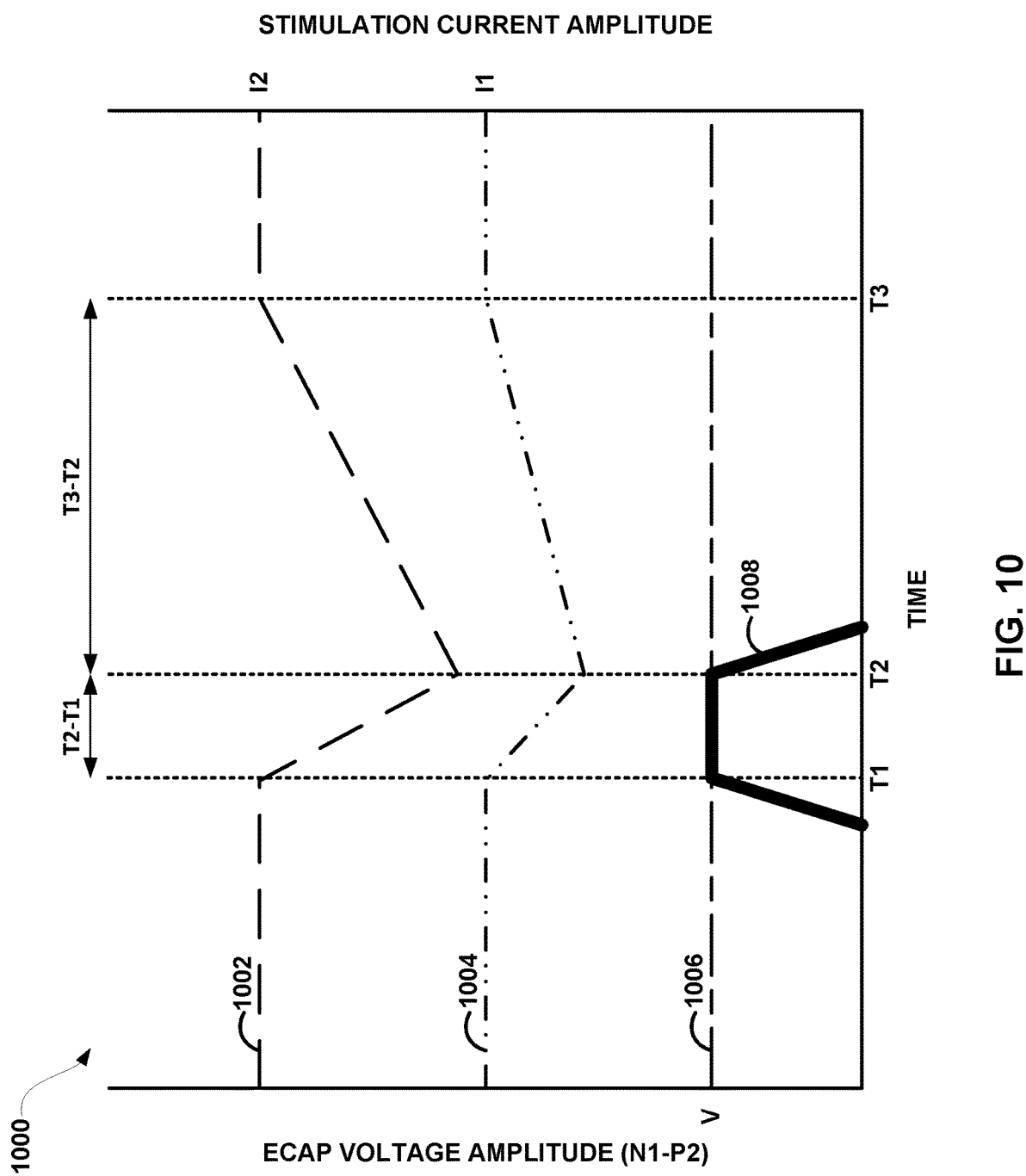
FIG. 10 is a graph illustrating a relationship between sensed ECAP voltage amplitude and stimulation current amplitude, in accordance with one or more techniques of this disclosure.

FIG. 10 illustrates a graph 1000 which plots control pulse current amplitude 1002, informed pulse current amplitude 1004, a threshold ECAP amplitude 1006, and an ECAP voltage amplitude 1008 as a function of time, in accordance with one or more techniques of this disclosure. For convenience, FIG. 10 is described with respect to IMD 200 of FIG. 2. However, the techniques of FIG. 10 may be performed by different components of IMD 200 or by additional or alternative medical devices.

Graph 1000 illustrates a relationship between sensed ECAP voltage amplitude 1008 and stimulation current amplitude. For example, control pulse current amplitude 1002 and informed pulse current amplitude 1004 are plotted alongside ECAP voltage amplitude 1008 as a function of time, thus showing how processing circuitry 208 of IMD 200 can change stimulation current amplitudes relative to ECAP voltage amplitude 1008. In some examples, IMD 200 delivers a plurality of control pulses and a plurality of informed pulses at control pulse current amplitude 1002 and informed pulse current amplitude 1004, respectively. Initially, IMD 200 may deliver a first set of control pulses, where IMD 200 delivers the first set of control pulses at current amplitude I2. Additionally, IMD 200 may deliver a first set of informed pulses, where IMD 200 delivers the first set of informed pulses at current amplitude I2. I1 and I2 may be referred to as a predetermined value for the amplitude of respective control and informed pulses, respectfully. This predetermined value may be a programmed value or otherwise selected value that a stimulation program has selected to at least partially define stimulation pulses to the patient in the absence of transient conditions (e.g., when the ECAP amplitude is below a threshold ECAP value). The first set of control pulses and the first set of informed pulses may be delivered prior to time T1. In some examples, I1 is 8 milliamps (mA) and I2 is 4 mA. Although control pulse current amplitude 1002 is shown as greater than informed pulse current amplitude 1004, control pulse current amplitude 1002 may be less than or the same as informed pulse current amplitude 1004 in other examples. In some examples, current amplitudes I1 and I2 may be less than 25 milliamps (mA) and can be between about 2 mA and about 18 mA. However, current amplitudes I1 and I2 may be any current amplitudes that IMD 200 can deliver to the patient and appropriate for eliciting ECAP signals and/or effective stimulation therapy for the patient.

While delivering the first set of control pulses and the first set of informed pulses, IMD 200 may record ECAP voltage amplitude 1008, which is a characteristic value derived from ECAP signals elicited from respective control pulses. During dynamic and transient conditions which occur in patient 102 such as coughing, sneezing, laughing, Valsalva maneuvers, leg lifting, cervical motions, or deep breathing, ECAP voltage amplitude 1008 may increase if control pulse current amplitude 1002 and informed pulse current amplitude 1004 are held constant. This increase in ECAP voltage amplitude 1008 may be caused by a reduction in the distance between the electrodes and nerves. For example, as illustrated in FIG. 10, ECAP voltage amplitude 1008 may increase prior to time T1 while stimulation current amplitude is held constant. An increasing ECAP voltage amplitude 1008 may indicate that patient 102 is at risk of experiencing transient overstimulation due to the control pulses and the informed pulses delivered by IMD 200. To prevent patient 102 from experiencing transient overstimulation, IMD 200 may decrease control pulse current amplitude 1002 and informed pulse current amplitude 1004 in response to ECAP voltage amplitude 1008 exceeding the threshold ECAP amplitude 1006. For example, if IMD 200 senses an ECAP having an ECAP voltage amplitude 1008 meeting or exceeding threshold ECAP amplitude 1006, as illustrated in FIG. 10 at time T1, IMD 200 may enter a decrement mode where control pulse current amplitude 1002 and informed pulse current amplitude 1004 are decreased. In some examples, the threshold ECAP amplitude 1006 is selected from a range of approximately 10 microvolts (µV) to approximately 100 µV, or from a range of approximately 15 microvolts (µV) to approximately 40 µV. For example, the threshold ECAP amplitude 1006 is 30 µV. In other examples, the threshold ECAP amplitude 1006 is less than or equal to 10 µV or greater than or equal to 100 µV. The exact value of threshold ECAP amplitude 1006 may depend on the patient's perception of the delivered stimulation, as well as the spacing between the sensing/stimulation electrodes and the neural tissue, whether or not stimulation intensity is increasing or decreasing, or other factors.

IMD 200 may respond relatively quickly to the ECAP voltage amplitude 1008 exceeding the threshold ECAP amplitude 1006. For example, IMD may be configured to detect threshold exceeding ECAP amplitudes within 20 milliseconds (ms). If IMD 200 delivers control pulses at a frequency of 50 Hz, the period of time for a single sample that includes delivering the control pulse and detecting the resulting ECAP signal may be 20 ms or less. However, since an ECAP signal may occur within one or two ms of delivery of the control pulse, IMD 200 may be configured to detect an ECAP signal exceeding the threshold ECAP amplitude in less than 10 ms. For transient conditions, such as a patient coughing or sneezing, these sampling periods would be sufficient to identify ECAP amplitudes exceeding the threshold and a responsive reduction in subsequent pulse amplitudes before the ECAP amplitude would have reached higher levels that may have been uncomfortable for the patient.

The decrement mode may, in some cases, be stored in storage device 216 of IMD 200. In the example illustrated in FIG. 10, the decrement mode is executed by IMD 200 over a second set of control pulses and a second set of informed pulses which occur between time T1 and time T2. In some examples, to execute the decrement mode, IMD 200 decreases the control pulse current amplitude 1002 of each control pulse of the second set of control pulses according to a first function with respect to time. In other words, IMD 200 decreases each consecutive control pulse of the second set of control pulses proportionally to an amount of time elapsed since a previous control pulse. Additionally, during the decrement mode, IMD 200 may decrease the informed pulse current amplitude 1004 of each informed pulse of the second set of informed pulses according to a second function with respect to time. Although linear first and second functions are shown, the first and/or second function may be non-linear, such as logarithmic (e.g., the rate of change decreases over time), exponential (e.g., the rate of change increases over time), parabolic, step-wise, multiple different functions, etc., in other examples. In some examples, processing circuitry 208 may select the first function or second function that defines the magnitude of each step in pulse amplitude change, or the rate of change, according to the detected posture state of the patient. For example, the first function or second function may represent a gain value or other function controlling the rate at which current amplitudes are changed. These functions selected according to the posture state may be used for the decrement and/or increment modes described herein. In some examples, processing circuitry 208 may select threshold ECAP amplitude 1006 based on the detected posture state of the patient. During a period of time in which IMD 200 is operating in the decrement mode (e.g., time interval T2-T1), ECAP voltage amplitude 1008 of ECAPs sensed by IMD 200 may be greater than or equal to threshold ECAP amplitude 1006.

In the example illustrated in FIG. 10, IMD 200 may sense an ECAP at time T2, where the ECAP has an ECAP voltage amplitude 1008 that falls back below the threshold ECAP amplitude 1006. The ECAP sensed at time T2 may, in some cases, be the first ECAP sensed by IMD 200 with a below-threshold amplitude since IMD 200 began the decrement mode at time T1. Based on sensing the ECAP at time T2, IMD 200 may deactivate the decrement mode and activate an increment mode. The increment mode may, in some cases, be stored in storage device 216 of IMD 200. IMD 200 may execute the increment mode over a third set of control pulses and a third set of informed pulses which occur between time T2 and time T3. In some examples, to execute the increment mode, IMD 200 increases the control pulse current amplitude 1002 of each control pulse of the third set of control pulses according to a third function with respect to time, which may be selected based on the detected posture state of the patient. In other words, IMD 200 increases each consecutive control pulse of the third set of control pulses proportionally to an amount of time elapsed since a previous control pulse. Additionally, during the increment mode, IMD 200 may increase the informed pulse current amplitude 1004 of each informed pulse of the third set of informed pulses according to a fourth function with respect to time.

As shown in FIG. 10, IMD 200 is configured to decrease amplitude at a faster rate than increasing amplitude after ECAP voltage amplitude 1008 falls below threshold ECAP amplitude 1006. In other examples, the rate of change during the decrement mode and increment mode may be similar. In other examples, IMD 200 may be configured to increase amplitude of informed and control pulses at a faster rate than when decreasing amplitude. The rate of change in amplitude of the pulses may be relatively instantaneously (e.g., a very fast rate) in other examples. As discussed above, the rate may be associated with a gain value for the detected posture state, such that the rate of increase or decrease in amplitude is faster for posture states having a shallower growth curve, or larger distance between the electrodes and target nerve. In one example, in response to ECAP voltage amplitude 1008 exceeding threshold ECAP amplitude 1006, IMD 200 may immediately drop the amplitude of one or both of control pulse current amplitude 1002 or informed pulse current amplitude 1004 to a predetermined or calculated value. Then, in response to ECAP voltage amplitude 1008 dropping back below threshold ECAP amplitude 1006, IMD 200 may enter increment mode as described above.

When control pulse current amplitude 1002 and informed pulse current amplitude 1004 return to current amplitude 12 and current amplitude I1, respectively, IMD 200 may deactivate the increment mode and deliver stimulation pulses at constant current amplitudes. By decreasing stimulation in response to ECAP amplitudes exceeding a threshold and subsequently increasing stimulation in response to ECAP amplitudes falling below the threshold, IMD 200 may prevent patient 105 from experiencing transient overstimulation or decrease a severity of transient overstimulation experienced by patient 105, whether the decrease is in terms of the length of the experience, the relative intensity, or both.

In other examples, processing circuitry 208 may only adjust stimulation parameters when the ECAP voltage amplitude 1008 is above an upper threshold or below a lower threshold. In this manner, when the ECAP voltage amplitude 1008 is between the upper ECAP amplitude threshold and the lower ECAP amplitude threshold, processing circuitry 208 does not increase the stimulation amplitude values back to the predetermined value or decrease the stimulation amplitude values. This "buffer" zone may reduce oscillating amplitude values when the ECAP amplitudes are similar to the ECAP amplitude threshold. These oscillating amplitude values may be perceived as uncomfortable or unwanted by the patient. However, once the ECAP amplitude drops below the lower ECAP amplitude threshold, processing circuitry 210 can return the amplitude value back to the predetermined amplitude value intended for therapy.

Although IMD 200 may increase and decrease the amplitudes by linear functions in some examples, IMD 200 may employ non-linear functions in other examples. For example, the gain value may represent a non-linear function in which the increment or decrement changes exponentially or logarithmically according to the difference between the sensed ECAP characteristic value and the threshold ECAP amplitude 1006. FIG. 10 is described in the situation in which IMD 200 delivers both control pulse and informed pulses. However, IMD 200 may apply the technique of FIG. 10 to the situation in which only control pulses are delivered to provide therapy to the patient. In this manner, IMD 200 would similarly enter a decrement mode or increment mode for control pulse current amplitude 1002 based on the detected ECAP voltage amplitude 1008 without adjusting the amplitude or other parameter of any other type of stimulation pulse.

Figure 11:
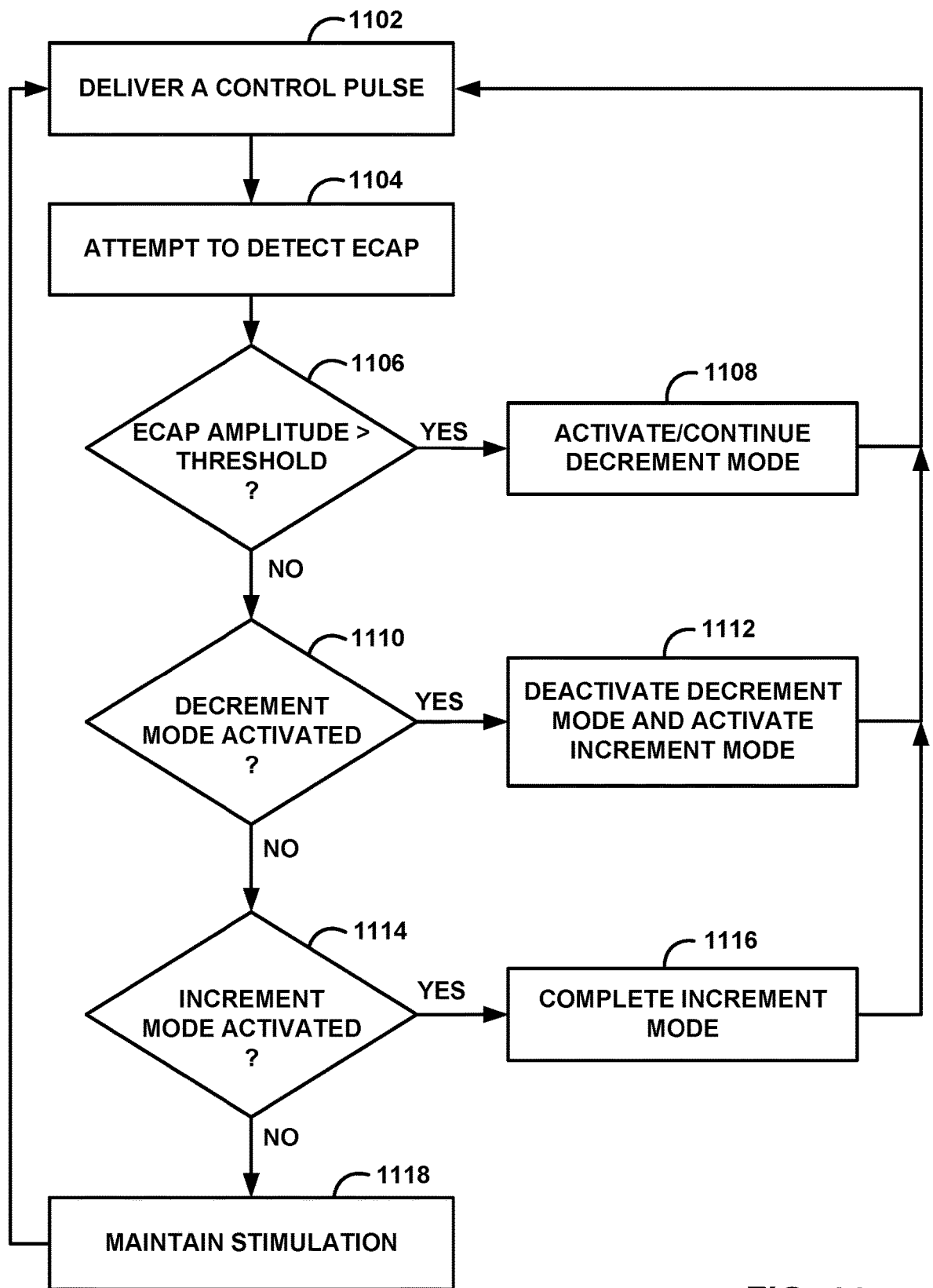
FIG. 11 is a flowchart illustrating an example operation for controlling stimulation therapy as described in FIG. 10.

FIG. 11 is a flow diagram illustrating an example operation for controlling stimulation based on one or more sensed ECAPs, in accordance with one or more techniques of this disclosure. For convenience, FIG. 11 is described with respect to IMD 200 of FIG. 2. However, the techniques of FIG. 11 may be performed by different components of IMD 200 or by additional or alternative medical devices. The technique of FIG. 11 is associated with graph 1000 of FIG. 10.

Stimulation generation circuitry 204 of IMD 200 may deliver electrical stimulation therapy to a patient (e.g., patient 102). In order to control the electrical stimulation therapy, processing circuitry 208 may direct the delivery of at least some stimulation pulses, where the electrical stimulation therapy may include a plurality of control pulses and/or informed pulses. Informed pulses may, in some cases, produce ECAPs detectable by IMD 200. However, in other cases, an electrical polarization of an informed pulse may interfere with sensing of an ECAP responsive to the informed pulse. In some examples, to evoke ECAPs which are detectable by IMD 200, stimulation generation circuitry 204 delivers a plurality of control pulses, the plurality of control pulses being interleaved with at least some informed pulses of the plurality of informed pulses. Processing circuitry 208 may control the delivery of control pulses according to instructions stored in memory 216. Since the control pulses may be interleaved with the informed pulses, sensing circuitry 206 of IMD 200 may detect a plurality of ECAPs, where sensing circuitry 206 is configured to detect each ECAP of the plurality of ECAPs after a control pulse of the plurality of control pulses and prior to a subsequent informed pulse of the plurality of informed pulses. In this way, IMD 200 may evoke the plurality of ECAPs in target tissue by delivering control pulses without the informed pulses obstructing IMD 200 from sensing the ECAPs.

As illustrated in FIG. 11, processing circuitry 208 directs stimulation generation circuitry 204 to deliver a control pulse (1102). Stimulation generation circuitry 204 may deliver the control pulse to target tissue of patient 102 via any combination of electrodes 232, 234 of leads 230. In some examples, the control pulse may include a balanced, bi-phasic square pulse that employs an active recharge phase. However, in other examples, the control pulse may include a monophasic pulse followed by a passive recharge phase. In other examples, the control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control pulse may have a pulse width of less than approximately 300 μs, such as a bi-phasic pulse with each phase having a duration of approximately 100 μs.

After delivering the control pulse, IMD 200 attempts to detect an ECAP (1104). For example, sensing circuitry 206 may monitor signals from any combination of electrodes 232, 234 of leads 230. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 102. In some examples, the particular combination of electrodes used for sensing ECAPs may be located on an opposite side of leads 230 from the particular combination of electrodes used to deliver stimulation pulses. IMD 200 may detect an ECAP responsive to the control pulse. IMD 200 may measure one or more characteristics of the responsive ECAP, such as ECAP amplitude, ECAP duration, peak-to-peak durations, or any combination thereof. For example, to measure an amplitude of the ECAP, IMD 200 may determine a voltage difference between an N1 ECAP peak and a P2 ECAP peak.

At block 1106, processing circuitry 208 determines if the ECAP amplitude of the responsive ECAP is greater than an ECAP amplitude threshold. If the ECAP amplitude is greater than the ECAP amplitude threshold ("YES" branch of block 1106), processing circuitry 208 activates/continues a decrement mode (1108) in IMD 200. For example, if the decrement mode is already "turned on" in IMD 200 when processing circuitry determines that the ECAP amplitude is greater than the ECAP amplitude threshold, then processing circuitry 208 maintains IMD 200 in the decrement mode. If the decrement mode is "turned off" in IMD 200 when processing circuitry determines that the ECAP amplitude is greater than the ECAP amplitude threshold, then processing circuitry 208 activates the decrement mode. In some examples, processing circuitry 208 may adjust the pulse amplitude according to a gain value or other factor selected according to the current posture state of the patient as determined by processing circuitry 208. The decrement mode may be a set of instructions which causes IMD 200 to decrease one or more parameter values of each consecutive informed pulse from a respective predetermined value (e.g., a value determined by a stimulation program and/or posture state) and decrease one or more parameter values of each consecutive control pulse from a respective predetermined value (e.g., a value determined by a stimulation program and/or posture state). In other words, the parameter values may be reduced from the values that IMD 200 would use to define respective pulses in the absence of the ECAP amplitude exceeding the threshold ECAP amplitude. For example, when the decrement mode is activated, processing circuitry 208 may decrease an electric current amplitude of each consecutive informed pulse delivered by IMD 200 and decrease an electric current amplitude of each consecutive control pulse delivered by IMD 200. After processing circuitry 208 activates/continues the decrement mode, the example operation may return to block 1102 and IMD 200 may deliver another control pulse.

If the ECAP amplitude is not greater than the ECAP amplitude threshold ("NO" branch of block 1106), processing circuitry 208 determines whether the decrement mode is activated in IMD 200 (1110). If the decrement mode is activated in IMD 200 ("YES" branch of block 1110), processing circuitry 208 deactivates the decrement mode and activates an increment mode (1112) in IMD 200. The increment mode may be a set of instructions which causes IMD 200 to increase one or more parameter values of each consecutive informed pulse and increase one or more parameter values of each consecutive control pulse. For example, when the increment mode is activated, processing circuitry 208 may increase an electric current amplitude of each consecutive informed pulse delivered by IMD 200 and increase an electric current amplitude of each consecutive control pulse delivered by IMD 200. In some examples, processing circuitry 208 may adjust the pulse amplitude according to a gain value or other factor selected according to the current posture state of the patient as determined by processing circuitry 208. After processing circuitry 208 deactivates the decrement mode and activates the increment mode, the example operation may return to block 1102 and IMD 200 may deliver another control pulse.

When the example operation of FIG. 11 arrives at block 1110 and the decrement mode is not activated in IMD 200 ("NO" branch of block 1110), processing circuitry 208 determines whether the increment mode is activated (1114) in IMD 200. If the increment mode is activated in IMD 200 ("YES" branch of block 1114), processing circuitry 208 may complete the increment mode (1116) in IMD 200. In some examples, to complete the increment mode, processing circuitry 208 may increase the electric current amplitude of each consecutive informed pulse delivered by IMD 200 and increase the electric current amplitude of each consecutive control pulse delivered by IMD 200 until the pulse amplitude of the stimulation pulses reach an electric current amplitude (e.g., a predetermined value that may be set by the stimulation program selected for therapy) of the stimulation pulses delivered by IMD 200 prior to the activation of the decrement mode. In this manner, the process may not be referred to as a fully closed-loop system. Put another way, IMD 200 may monitor the high end (ECAP amplitude threshold) for adjusting stimulation pulses instead of monitoring any low end of the sensed ECAP amplitude. For example, IMD 20 may continue to increase the current amplitude of consecutive informed pulses without any feedback from the sensed ECAP, unless the sensed ECAP value again exceeds the ECAP amplitude threshold. After processing circuitry 208 completes the increment mode, the example operation may return to block 1102 and IMD 200 may deliver another control pulse. When the example operation of FIG. 11 arrives at block 1114 and the increment mode is not activated in IMD 200 ("NO" branch of block 1114), processing circuitry 208 maintains stimulation (1118) in IMD 200. Although FIG. 11 describes adjusting both informed pulses and control pulses, the technique of FIG. 11 may also apply when IMD 200 is delivering only control pulses (e.g., without informed pulses) to the patient for therapy.

The following examples are described herein. Example 1: a system comprising: sensing circuitry configured to sense an evoked compound action potential (ECAP) signal elicited by a control stimulation pulse of a plurality of control stimulation pulses; and processing circuitry configured to: control delivery of a first informed stimulation pulse defined by at least a first value of an informed stimulation parameter, the informed stimulation pulse being one informed stimulation pulse of a plurality of informed stimulation pulse; control delivery of the control stimulation pulse to a patient, the control stimulation pulse defined by at least a first value of a control stimulation parameter; determine a characteristic value of the ECAP signal elicited from the control stimulation pulse; receive, from a sensor, a posture state signal representing a posture state of the patient; adjust, based on the characteristic value of the ECAP signal and the posture state signal, the first value of the informed stimulation parameter to a second value of the informed stimulation parameter; and control delivery of a second informed stimulation pulse of the plurality of informed stimulation pulses that is defined at least by the second value of the informed stimulation parameter.

Example 2: the system of example 1, further comprising stimulation generation circuitry configured to deliver the plurality of control stimulation pulses and the plurality of informed stimulation pulses to the patient, and wherein the processing circuitry is configured to control the stimulation generation circuitry to deliver the plurality of control stimulation pulses and the plurality of informed stimulation pulses.

Example 3: the system of any of examples 1 or 2, wherein the informed stimulation parameter and the control stimulation parameter comprises one of an amplitude, a pulse width, or a pulse shape.

Example 4: the system of any of examples 1 through 3, wherein the processing circuitry is configured to: determine, based on the posture state signal, a gain value for the posture state; and adjust the first value of the informed stimulation pulse to the second value of the informed stimulation pulse by one of increasing or decreasing the stimulation parameter of the electrical stimulation based on the gain value associated with the posture state of the patient.

Example 5: the system of example 4, wherein the characteristic value is an amplitude of a portion of the ECAP signal, wherein the informed stimulation parameter comprises an informed amplitude, wherein the control stimulation parameter comprises a control amplitude, and wherein the processing circuitry is configured to adjust the first value of the informed stimulation pulse to the second value of the informed stimulation pulse by: subtracting the amplitude from a target ECAP amplitude value for the patient to generate a differential amplitude; multiplying the differential amplitude by the gain value to generate a preliminary differential value; multiplying the preliminary differential value by a scaling factor to generate an informed differential value, wherein the scaling factor represents a ratio of the first value of the informed amplitude that defines the first informed stimulation pulse delivered prior to the control stimulation pulse to a control amplitude defining the control stimulation pulse; adding the informed differential value to the first value of the informed amplitude to generate the second value of the informed amplitude that at least partially defines the electrical stimulation to be delivered to the patient; and adding the preliminary differential value to the first value of the control stimulation parameter to generate a second value of the control stimulation parameter for a subsequent control stimulation pulse of the plurality of control stimulation pulses.

Example 6: the system of example 5, wherein the amplitude of the portion of the ECAP signal comprises a voltage amplitude between an N1 peak and a P2 peak of the ECAP signal.

Example 7: the system of any of examples 4 through 6, wherein the gain value is inversely proportional to a slope of a growth curve defining a relationship of ECAP values to values of the control stimulation parameter for the patient.

Example 8: the system of example 7, wherein the posture state is one posture state of a plurality of posture states, and wherein each posture state comprises a respective growth curve representing the relationship between the ECAP values and the values of the control parameter when the patient occupies that posture state.

Example 9: the system of any of examples 1 through 8, wherein the processing circuitry is configured to adjust the first value of the informed stimulation parameter to the second value of the informed stimulation parameter by: comparing the characteristic value of the ECAP signal to a threshold ECAP characteristic value; determining that the characteristic value of the ECAP signal is greater than the threshold ECAP characteristic value; and responsive to determining that the characteristic value of the ECAP signal is greater than the threshold ECAP characteristic value, decreasing the first value of the informed stimulation parameter to the second value of the informed stimulation parameter.

Example 10: the system of example 9, wherein the ECAP signal is a first ECAP signal and the characteristic value is a first characteristic value, wherein the control stimulation pulse is a first control stimulation pulse, and wherein the processing circuitry is configured to: determine a second characteristic value of a second ECAP signal elicited from a second stimulation pulse delivered after sensing the first ECAP signal; determine that the second characteristic value of the second ECAP signal subsequently decreased below the threshold ECAP characteristic value; and responsive to determining that the second characteristic value of the second ECAP signal decreases below the threshold ECAP characteristic value, increase the second value of the informed stimulation parameter to a third value of the informed stimulation parameter, the third value of the informed stimulation parameter being limited to be less than or equal to the first value.

Example 11: the system of example 10, wherein the processing circuitry is configured to increase the second value of the informed stimulation parameter at a slower rate than the first value of the informed stimulation parameter was decreased to the second value of the informed stimulation parameter.

Example 12: the system of any of examples 1 through 11, wherein the processing circuitry is configured to select, based on the posture state signal, the gain value from a plurality of gain values associated with respective posture states, and wherein the gain value represents at least one of an increment rate or a decrement rate for at least one of the informed stimulation parameter or the control stimulation parameter.

Example 13: the system of any of examples 1 through 12, wherein the processing circuitry is configured to: select, based on the posture state signal, a target ECAP characteristic value; compare the characteristic value of the ECAP signal to the threshold ECAP characteristic value; adjust, based on the comparison of the characteristic value of the ECAP signal to the threshold ECAP characteristic value and a gain value, the first value of the informed stimulation parameter to the second value of the informed stimulation parameter.

Example 14: the system of any of examples 1 through 13, wherein the processing circuitry is configured to: determine, from at least the posture state signal representing the posture state of the patient, that the posture state of the patient has changed; and responsive to determining that the posture state has changed, change an ECAP sensing frequency.

Example 15: the system of any of examples 1 through 14, further comprising an implantable medical device comprising the sensing circuitry and the processing circuitry.

Example 16: the system of any of examples 1 through 15, wherein the plurality of informed stimulation pulses are defined by an informed pulse width greater than approximately 300 microseconds and less than approximately 1000 microseconds, and wherein the plurality of control stimulation pulses are defined by a control pulse width less than approximately 300 microseconds.

Example 17: a method comprising: controlling, by processing circuitry, delivery of a first informed stimulation pulse defined by at least a first value of an informed stimulation parameter, the informed stimulation pulse being one informed stimulation pulse of a plurality of informed stimulation pulse; controlling, by the processing circuitry, delivery of a control stimulation pulse of a plurality of control stimulation pulses to a patient, the control stimulation pulse defined by at least a first value of a control stimulation parameter; sensing, by sensing circuitry, an evoked compound action potential (ECAP) signal elicited by the control stimulation pulse; determining, by the processing circuitry, a characteristic value of the ECAP signal elicited from the control stimulation pulse; receiving, by the processing circuitry and from a sensor, a posture state signal representing a posture state of the patient; adjusting, by the processing circuitry and based on the characteristic value of the ECAP signal and the posture state signal, the first value of the informed stimulation parameter to a second value of the informed stimulation parameter; and controlling, by the processing circuitry, delivery of a second informed stimulation pulse of the plurality of informed stimulation pulses that is defined at least by the second value of the informed stimulation parameter.

Example 18: the method of example 17, further comprising delivering, by stimulation generation circuitry, the plurality of control stimulation pulses and the plurality of informed stimulation pulses to the patient.

Example 19: the method of any of examples 17 and 18, wherein the informed stimulation parameter and the control stimulation parameter comprises one of an amplitude, a pulse width, or a pulse shape.

Example 20: the method of any of examples 17 through 19, further comprising determining, based on the posture state signal, a gain value for the posture state, wherein adjusting the first value of the informed stimulation pulse to the second value of the informed stimulation pulse comprises one of increasing or decreasing the stimulation parameter of the electrical stimulation based on the gain value associated with the posture state of the patient.

Example 21: the method of example 20, wherein the characteristic value is an amplitude of a portion of the ECAP signal, wherein the informed stimulation parameter comprises an informed amplitude, wherein the control stimulation parameter comprises a control amplitude, and wherein adjusting the first value of the informed stimulation pulse to the second value of the informed stimulation pulse comprises: subtracting the amplitude from a target ECAP amplitude value for the patient to generate a differential amplitude; multiplying the differential amplitude by the gain value to generate a preliminary differential value; multiplying the preliminary differential value by a scaling factor to generate an informed differential value, wherein the scaling factor represents a ratio of the first value of the informed amplitude that defines the first informed stimulation pulse delivered prior to the control stimulation pulse to a control amplitude defining the control stimulation pulse; adding the informed differential value to the first value of the informed amplitude to generate the second value of the informed amplitude that at least partially defines the electrical stimulation to be delivered to the patient; and adding the preliminary differential value to the first value of the control stimulation parameter to generate a second value of the control stimulation parameter for a subsequent control stimulation pulse of the plurality of control stimulation pulses.

Example 22: the method of example 21, wherein the amplitude of the portion of the ECAP signal comprises a voltage amplitude between an N1 peak and a P2 peak of the ECAP signal.

Example 23: the method of any of examples 20 through 22, wherein the gain value is inversely proportional to a slope of a growth curve defining a relationship of ECAP values to values of the control stimulation parameter for the patient.

Example 24: the method of example 23, wherein the posture state is one posture state of a plurality of posture states, and wherein each posture state comprises a respective growth curve representing the relationship between the ECAP values and the values of the control parameter when the patient occupies that posture state.

Example 25: the method of any of examples 17 through 24, wherein adjusting the first value of the informed stimulation parameter to the second value of the informed stimulation parameter comprises: comparing the characteristic value of the ECAP signal to a threshold ECAP characteristic value; determining that the characteristic value of the ECAP signal is greater than the threshold ECAP characteristic value; and responsive to determining that the characteristic value of the ECAP signal is greater than the threshold ECAP characteristic value, decreasing the first value of the informed stimulation parameter to the second value of the informed stimulation parameter.

Example 26: the method of example 25, wherein the ECAP signal is a first ECAP signal and the characteristic value is a first characteristic value, wherein the control stimulation pulse is a first control stimulation pulse, and wherein the method further comprises: determining a second characteristic value of a second ECAP signal elicited from a second stimulation pulse delivered after sensing the first ECAP signal; determining that the second characteristic value of the second ECAP signal subsequently decreased below the threshold ECAP characteristic value; and responsive to determining that the second characteristic value of the second ECAP signal decreases below the threshold ECAP characteristic value, increasing the second value of the informed stimulation parameter to a third value of the informed stimulation parameter, the third value of the informed stimulation parameter being limited to be less than or equal to the first value.

Example 27: the method of example 26, further comprising increasing the second value of the informed stimulation parameter at a slower rate than the first value of the informed stimulation parameter was decreased to the second value of the informed stimulation parameter.

Example 28: the method of any of examples 17 through 27, further comprising selecting, based on the posture state signal, the gain value from a plurality of gain values associated with respective posture states, and wherein the gain value represents at least one of an increment rate or a decrement rate for at least one of the informed stimulation parameter or the control stimulation parameter.

Example 29: the method of any of examples 17 through 28, further comprising: selecting, based on the posture state signal, a target ECAP characteristic value; comparing the characteristic value of the ECAP signal to the threshold ECAP characteristic value; and adjusting, based on the comparison of the characteristic value of the ECAP signal to the threshold ECAP characteristic value and a gain value, the first value of the informed stimulation parameter to the second value of the informed stimulation parameter.

Example 30: the method of any of examples 17 through 29, further comprising: determining, from at least the posture state signal representing the posture state of the patient, that the posture state of the patient has changed; and responsive to determining that the posture state has changed, changing an ECAP sensing frequency.

Example 31: the method of any of examples 17 through 30, wherein an implantable medical device comprises the sensing circuitry and the processing circuitry.

Example 32: the method of any of examples 17 through 31, wherein the plurality of informed stimulation pulses are defined by an informed pulse width greater than approximately 300 microseconds and less than approximately 1000 microseconds, and wherein the plurality of control stimulation pulses are defined by a control pulse width less than approximately 300 microseconds.

Example 33: a computer-readable storage medium comprising instructions that, when executed by processing circuitry, cause the processing circuitry to: control delivery of a first informed stimulation pulse defined by at least a first value of an informed stimulation parameter, the informed stimulation pulse being one informed stimulation pulse of a plurality of informed stimulation pulse; control delivery of a control stimulation pulse of a plurality of control stimulation pulses to a patient, the control stimulation pulse defined by at least a first value of a control stimulation parameter; control sensing circuitry to sense an evoked compound action potential (ECAP) signal elicited by the control stimulation pulse; determine a characteristic value of the ECAP signal elicited from the control stimulation pulse; receive, from a sensor, a posture state signal representing a posture state of the patient; adjust, based on the characteristic value of the ECAP signal and the posture state signal, the first value of the informed stimulation parameter to a second value of the informed stimulation parameter; and control delivery of a second informed stimulation pulse of the plurality of informed stimulation pulses that is defined at least by the second value of the informed stimulation parameter.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
sensing circuitry configured to sense an evoked compound action potential (ECAP) signal elicited by a control stimulation pulse of a plurality of control stimulation pulses; and
processing circuitry configured to:
control delivery of a first informed stimulation pulse defined by at least a first value of a stimulation parameter, the first informed stimulation pulse being one informed stimulation pulse of a plurality of informed stimulation pulses at a frequency over a period of time;
control delivery of the control stimulation pulse to a patient as part of the plurality of control stimulation pulses interleaved with at least some informed pulses of the plurality of informed stimulation pulses during the period of time, the control stimulation pulse defined by at least a second value of the stimulation parameter, wherein the first value of the stimulation parameter is different than the second value of the stimulation parameter;
determine a characteristic value of the ECAP signal elicited from the control stimulation pulse;
receive, from a sensor, a posture state signal representing a posture state of the patient;
adjust, based on the characteristic value of the ECAP signal and the posture state signal, the first value of the stimulation parameter to a third value of the stimulation parameter; and
control delivery of a second informed stimulation pulse of the plurality of informed stimulation pulses that is defined at least by the third value of the stimulation parameter.

2. The system of claim 1, further comprising stimulation generation circuitry configured to deliver the plurality of control stimulation pulses and the plurality of informed stimulation pulses to the patient, and wherein the processing circuitry is configured to control the stimulation generation circuitry to deliver the plurality of control stimulation pulses and the plurality of informed stimulation pulses.

3. The system of claim 1, wherein the stimulation parameter comprises one of an amplitude, a pulse width, or a pulse shape.

4. The system of claim 1, wherein the processing circuitry is configured to:
determine, based on the posture state signal, a gain value for the posture state; and adjust the first value of the stimulation parameter of the first informed stimulation pulse to the third value of the stimulation parameter of the second informed stimulation pulse by one of increasing or decreasing the stimulation parameter of the electrical stimulation based on the gain value associated with the posture state of the patient.

5. The system of claim 4, wherein the characteristic value is an amplitude of a portion of the ECAP signal, wherein the stimulation parameter comprises an amplitude, and wherein the processing circuitry is configured to adjust the first value of the first informed stimulation pulse to the third value of the second informed stimulation pulse by at least:
  subtracting the amplitude from a target ECAP amplitude value for the patient to generate a differential amplitude;
  multiplying the differential amplitude by the gain value to generate a preliminary differential value;
  multiplying the preliminary differential value by a scaling factor to generate an informed differential value, wherein the scaling factor represents a ratio of the first value of the amplitude that defines the first informed stimulation pulse delivered prior to the control stimulation pulse to the second value of the amplitude defining the control stimulation pulse;
  adding the informed differential value to the first value of the informed amplitude to generate the third value of the amplitude that at least partially defines the electrical stimulation to be delivered to the patient; and
  adding the preliminary differential value to the second value of the amplitude to generate a fourth value of the amplitude for a subsequent control stimulation pulse of the plurality of control stimulation pulses.

6. The system of claim 5, wherein the amplitude of the portion of the ECAP signal comprises a voltage amplitude between an N1 peak and a P2 peak of the ECAP signal.

7. The system of claim 4, wherein the gain value is inversely proportional to a slope of a growth curve defining a relationship of ECAP values to values of the stimulation parameter for the patient.

8. The system of claim 7, wherein the posture state is one posture state of a plurality of posture states, and wherein each posture state comprises a respective growth curve representing the relationship between the ECAP values and the values of the stimulation parameter when the patient occupies that posture state.

9. The system of claim 1, wherein the processing circuitry is configured to adjust the first value of the stimulation parameter to the third value of the stimulation parameter by:
  comparing the characteristic value of the ECAP signal to a threshold ECAP characteristic value;
  determining that the characteristic value of the ECAP signal is greater than the threshold ECAP characteristic value; and
  responsive to determining that the characteristic value of the ECAP signal is greater than the threshold ECAP characteristic value, decreasing the first value of the stimulation parameter to the third value of the stimulation parameter.

10. The system of claim 9, wherein the ECAP signal is a first ECAP signal and the characteristic value is a first characteristic value, wherein the control stimulation pulse is a first control stimulation pulse, and wherein the processing circuitry is configured to:
  determine a second characteristic value of a second ECAP signal elicited from a second stimulation pulse delivered after sensing the first ECAP signal;
  determine that the second characteristic value of the second ECAP signal subsequently decreased below the threshold ECAP characteristic value; and
  responsive to determining that the second characteristic value of the second ECAP signal decreased below the threshold ECAP characteristic value, increase the third value of the stimulation parameter to a fourth value of the informed stimulation parameter, the fourth value of the stimulation parameter being limited to be less than or equal to the first value.

11. The system of claim 10, wherein the processing circuitry is configured to increase the third value of the stimulation parameter at a slower rate than the first value of the stimulation parameter was decreased to the third value of the stimulation parameter.

12. The system of claim 1, wherein the processing circuitry is configured to select, based on the posture state signal, a gain value from a plurality of gain values associated with respective posture states, and wherein the gain value represents at least one of an increment rate or a decrement rate for the stimulation parameter defining at least one of the plurality of control stimulation pulses or the plurality of informed stimulation pulses.

13. The system of claim 1, wherein the processing circuitry is configured to:
  select, based on the posture state signal, a target ECAP characteristic value;
  compare the characteristic value of the ECAP signal to the threshold ECAP characteristic value;
  adjust, based on the comparison of the characteristic value of the ECAP signal to the threshold ECAP characteristic value and a gain value, the first value of the stimulation parameter to the third value of the stimulation parameter.

14. The system of claim 1, wherein the processing circuitry is configured to:
  determine, from at least the posture state signal representing the posture state of the patient, that the posture state of the patient has changed; and
  responsive to determining that the posture state has changed, change an ECAP sensing frequency.

15. The system of claim 1, further comprising an implantable medical device comprising the sensing circuitry and the processing circuitry.

16. The system of claim 1, wherein the plurality of informed stimulation pulses are defined by an informed pulse width greater than approximately 300 microseconds and less than approximately 1000 microseconds, and wherein the plurality of control stimulation pulses are defined by a control pulse width less than approximately 300 microseconds.

17. A method comprising:
  controlling, by processing circuitry, delivery of a first informed stimulation pulse defined by at least a first value of a stimulation parameter, the first informed stimulation pulse being one informed stimulation pulse of a plurality of informed stimulation pulses at a frequency over a period of time;
  controlling, by the processing circuitry, delivery of a control stimulation pulse of a plurality of control stimulation pulses to a patient interleaved with at least some informed pulses of the plurality of informed stimulation pulses during the period of time, the control stimulation pulse defined by at least a second value of the stimulation parameter, wherein the first value of the stimulation parameter is different than the second value of the stimulation parameter;

sensing, by sensing circuitry, an evoked compound action potential (ECAP) signal elicited by the control stimulation pulse;

determining, by the processing circuitry, a characteristic value of the ECAP signal elicited from the control stimulation pulse;

receiving, by the processing circuitry and from a sensor, a posture state signal representing a posture state of the patient;

adjusting, by the processing circuitry and based on the characteristic value of the ECAP signal and the posture state signal, the first value of the stimulation parameter to a third value of the stimulation parameter; and controlling, by the processing circuitry, delivery of a second informed stimulation pulse of the plurality of informed stimulation pulses that is defined at least by the third value of the stimulation parameter.

18. The method of claim 17, further comprising delivering, by stimulation generation circuitry, the plurality of control stimulation pulses and the plurality of informed stimulation pulses to the patient.

19. The method of claim 17, wherein the stimulation parameter comprises one of an amplitude, a pulse width, or a pulse shape.

20. The method of claim 17, further comprising determining, based on the posture state signal, a gain value for the posture state, wherein adjusting the first value of the stimulation parameter of the first informed stimulation pulse to the third value of the stimulation parameter of the second informed stimulation pulse comprises one of increasing or decreasing the stimulation parameter of the electrical stimulation based on the gain value associated with the posture state of the patient.

21. The method of claim 20, wherein the characteristic value is an amplitude of a portion of the ECAP signal, wherein the stimulation parameter comprises an amplitude, and wherein adjusting the first value of the informed stimulation pulse to the third value of the second informed stimulation pulse comprises:

subtracting the amplitude from a target ECAP amplitude value for the patient to generate a differential amplitude;

multiplying the differential amplitude by the gain value to generate a preliminary differential value;

multiplying the preliminary differential value by a scaling factor to generate an informed differential value, wherein the scaling factor represents a ratio of the first value of the amplitude that defines the first informed stimulation pulse delivered prior to the control stimulation pulse to the second value of the amplitude defining the control stimulation pulse;

adding the informed differential value to the first value of the amplitude to generate the third value of the amplitude that at least partially defines the electrical stimulation to be delivered to the patient; and adding the preliminary differential value to the second value of the amplitude to generate a fourth value of the amplitude for a subsequent control stimulation pulse of the plurality of control stimulation pulses.

22. The method of claim 21, wherein the amplitude of the portion of the ECAP signal comprises a voltage amplitude between an N1 peak and a P2 peak of the ECAP signal.

23. The method of claim 20, wherein the gain value is inversely proportional to a slope of a growth curve defining a relationship of ECAP values to values of the stimulation parameter for the patient.

24. The method of claim 23, wherein the posture state is one posture state of a plurality of posture states, and wherein each posture state comprises a respective growth curve representing the relationship between the ECAP values and the values of the stimulation parameter when the patient occupies that posture state.

25. The method of claim 17, wherein adjusting the first value of the stimulation parameter to the third value of the stimulation parameter comprises:

comparing the characteristic value of the ECAP signal to a threshold ECAP characteristic value;

determining that the characteristic value of the ECAP signal is greater than the threshold ECAP characteristic value; and responsive to determining that the characteristic value of the ECAP signal is greater than the threshold ECAP characteristic value, decreasing the first value of the stimulation parameter to the third value of the stimulation parameter.

26. The method of claim 25, wherein the ECAP signal is a first ECAP signal and the characteristic value is a first characteristic value, wherein the control stimulation pulse is a first control stimulation pulse, and wherein the method further comprises:

determining a second characteristic value of a second ECAP signal elicited from a second stimulation pulse delivered after sensing the first ECAP signal;

determining that the second characteristic value of the second ECAP signal subsequently decreased below the threshold ECAP characteristic value; and responsive to determining that the second characteristic value of the second ECAP signal decreases below the threshold ECAP characteristic value, increasing the third value of the stimulation parameter to a fourth value of the stimulation parameter, the fourth value of the stimulation parameter being limited to be less than or equal to the first value.

27. The method of claim 26, further comprising increasing the third value of the stimulation parameter at a slower rate than the first value of the stimulation parameter was decreased to the third value of the stimulation parameter.

28. The method of claim 17, further comprising selecting, based on the posture state signal, a gain value from a plurality of gain values associated with respective posture states, and wherein the gain value represents at least one of an increment rate or a decrement rate for the stimulation parameter defining at least one of the plurality of control stimulation pulses or the plurality of informed stimulation pulses.

29. The method of claim 17, further comprising:

selecting, based on the posture state signal, a target ECAP characteristic value;

comparing the characteristic value of the ECAP signal to the threshold ECAP characteristic value; and adjusting, based on the comparison of the characteristic value of the ECAP signal to the threshold ECAP characteristic value and a gain value, the first value of the stimulation parameter to the third value of the stimulation parameter.

30. The method of claim 17, further comprising:

determining, from at least the posture state signal representing the posture state of the patient, that the posture state of the patient has changed; and responsive to determining that the posture state has changed, changing an ECAP sensing frequency.

31. The method of claim 17, wherein an implantable medical device comprises the sensing circuitry and the processing circuitry.

32. The method of claim 17, wherein the plurality of informed stimulation pulses are defined by an informed pulse width greater than approximately 300 microseconds and less than approximately 1000 microseconds, and wherein the plurality of control stimulation pulses are defined by a control pulse width less than approximately 300 microseconds.

33. A computer-readable storage medium comprising instructions that, when executed by processing circuitry, cause the processing circuitry to:
 control delivery of a first informed stimulation pulse defined by at least a first value of a stimulation parameter, the informed stimulation pulse being one informed stimulation pulse of a plurality of informed stimulation pulses at a frequency over a period of time;
 control delivery of a control stimulation pulse of a plurality of control stimulation pulses to a patient interleaved with at least some informed pulses of the plurality of informed stimulation pulses during the period of time, the control stimulation pulse defined by at least a second value of the stimulation parameter, wherein the first value of the stimulation parameter is different than the second value of the stimulation parameter;
 control sensing circuitry to sense an evoked compound action potential (ECAP) signal elicited by the control stimulation pulse;
 determine a characteristic value of the ECAP signal elicited from the control stimulation pulse;
 receive, from a sensor, a posture state signal representing a posture state of the patient;
 adjust, based on the characteristic value of the ECAP signal and the posture state signal, the first value of the stimulation parameter to a third value of the stimulation parameter; and
 control delivery of a second informed stimulation pulse of the plurality of informed stimulation pulses that is defined at least by the third value of the stimulation parameter.

\* \* \* \* \*